United States Patent
Tabor et al.

(10) Patent No.: US 9,526,627 B2
(45) Date of Patent: Dec. 27, 2016

(54) EXPANDABLE INTERBODY DEVICE SYSTEM AND METHOD

(71) Applicant: Exactech, Inc., Gainesville, FL (US)

(72) Inventors: Derek A. Tabor, Alachua, FL (US); Larry G. Hickey, Alachua, FL (US)

(73) Assignee: Exactech, Inc., Gainesville, FL (US)

( * ) Notice: Subject to any disclaimer, the term of this patent is extended or adjusted under 35 U.S.C. 154(b) by 0 days.

(21) Appl. No.: 13/678,238

(22) Filed: Nov. 15, 2012

(65) Prior Publication Data

US 2013/0158667 A1    Jun. 20, 2013

Related U.S. Application Data

(60) Provisional application No. 61/561,037, filed on Nov. 17, 2011.

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/4611* (2013.01); *A61F 2002/305* (2013.01); *A61F 2002/30387* (2013.01); *A61F 2002/30482* (2013.01); *A61F 2002/30556* (2013.01); *A61F 2002/30616* (2013.01); *A61F 2002/30772* (2013.01); *A61F 2002/30904* (2013.01); *A61F 2002/448* (2013.01)

(58) Field of Classification Search
CPC .............................. A61F 2/4455; A61F 2/4611
USPC ........................... 623/17.11–17.16; 606/86 A
See application file for complete search history.

(56) References Cited

U.S. PATENT DOCUMENTS

| | | | |
|---|---|---|---|
| 3,848,601 A | 11/1974 | Ma et al. | |
| 3,867,728 A | 2/1975 | Stubstad et al. | |
| 4,309,777 A | 1/1982 | Patil | |
| 4,349,921 A | 9/1982 | Kuntz | |
| 4,611,581 A | 9/1986 | Steffee | |
| 4,657,550 A | 4/1987 | Daher | |
| 4,696,290 A | 9/1987 | Steffee | |

(Continued)

FOREIGN PATENT DOCUMENTS

WO    2007035892    3/2007

*Primary Examiner* — Christopher Beccia
(74) *Attorney, Agent, or Firm* — Meyertons, Hood, Kivlin, Kowert & Goetzel, P.C.; Eric B. Meyertons

(57) ABSTRACT

Provided is an intervertebral implant to be implanted within an intervertebral space between endplates of adjacent vertebra during use. The implant includes an upper member having an inferior surface including an upper guide track and a superior surface to contact an endplate of an upper one of the adjacent vertebra during use, a lower member having a superior surface including a lower guide track and an inferior surface to contact an endplate of a lower one of the adjacent vertebra during use, and an insert having a superior surface including an upper guide rail to engage the upper guide track during use and an inferior surface including a lower guide rail to engage the lower guide track during use. Engagement of the upper and lower guide rails with the upper and lower guide tracks, respectively, guides insertion of the insert between the upper and lower members during use, and insertion of the insert between the upper and lower members facilitates expansion of the intervertebral implant.

19 Claims, 13 Drawing Sheets

(56) References Cited

U.S. PATENT DOCUMENTS

| | | |
|---|---|---|
| 4,743,260 A | 5/1988 | Burton |
| 4,759,766 A | 7/1988 | Buettner-Janz et al. |
| 4,759,769 A | 7/1988 | Hedman et al. |
| 4,763,644 A | 8/1988 | Webb |
| 4,772,287 A | 9/1988 | Ray et al. |
| 4,790,303 A | 12/1988 | Steffee |
| 4,854,311 A | 8/1989 | Steffee |
| 4,863,476 A | 9/1989 | Shepperd |
| 4,863,477 A | 9/1989 | Monson |
| 4,907,577 A | 3/1990 | Wu |
| 4,911,718 A | 3/1990 | Lee et al. |
| 4,932,975 A | 6/1990 | Main et al. |
| 4,946,378 A | 8/1990 | Hirayama et al. |
| 4,946,458 A | 8/1990 | Harms et al. |
| 5,042,982 A | 8/1991 | Harms et al. |
| 5,047,055 A | 9/1991 | Bao et al. |
| 5,059,194 A | 10/1991 | Michelson |
| 5,071,437 A | 12/1991 | Steffee |
| 5,092,867 A | 3/1992 | Harms et al. |
| 5,108,438 A | 4/1992 | Stone |
| 5,123,926 A | 6/1992 | Pisharodi |
| 5,171,278 A | 12/1992 | Pisharodi |
| 5,171,281 A | 12/1992 | Parsons et al. |
| 5,180,393 A | 1/1993 | Commarmond |
| 5,192,326 A | 3/1993 | Bao et al. |
| 5,196,013 A | 3/1993 | Harms et al. |
| 5,207,678 A | 5/1993 | Harms et al. |
| 5,217,497 A | 6/1993 | Mehdian |
| 5,246,458 A | 9/1993 | Graham |
| 5,258,031 A | 11/1993 | Salib et al. |
| 5,261,909 A | 11/1993 | Sutterlin et al. |
| 5,306,307 A | 4/1994 | Senter et al. |
| 5,306,309 A | 4/1994 | Wagner et al. |
| 5,314,477 A | 5/1994 | Marnay |
| 5,320,644 A | 6/1994 | Baumgartner |
| 5,336,223 A | 8/1994 | Rogers |
| 5,370,697 A | 12/1994 | Baumgartner |
| 5,375,823 A | 12/1994 | Navas |
| 5,397,364 A | 3/1995 | Kozak et al. |
| 5,401,269 A | 3/1995 | Buettner-Janz et al. |
| 5,403,315 A | 4/1995 | Ashman |
| 5,415,661 A | 5/1995 | Holmes |
| 5,423,816 A | 6/1995 | Lin |
| 5,425,773 A | 6/1995 | Boyd et al. |
| 5,443,467 A | 8/1995 | Biedermann et al. |
| 5,458,642 A | 10/1995 | Beer et al. |
| 5,458,643 A | 10/1995 | Oka et al. |
| 5,480,401 A | 1/1996 | Navas |
| 5,496,321 A | 3/1996 | Puno et al. |
| 5,498,263 A | 3/1996 | DiNello et al. |
| 5,507,816 A | 4/1996 | Bullivant |
| 5,514,132 A | 5/1996 | Csernatony et al. |
| 5,514,180 A | 5/1996 | Heggeness et al. |
| 5,522,899 A | 6/1996 | Michelson |
| 5,527,314 A | 6/1996 | Brumfield et al. |
| 5,534,028 A | 7/1996 | Bao et al. |
| 5,534,029 A | 7/1996 | Shima |
| 5,534,030 A | 7/1996 | Navarro et al. |
| 5,540,688 A | 7/1996 | Navas |
| 5,545,165 A | 8/1996 | Biedermann et al. |
| 5,554,191 A | 9/1996 | Lahille et al. |
| 5,556,431 A | 9/1996 | Buttner-Janz |
| 5,562,663 A | 10/1996 | Wisnewski et al. |
| 5,562,737 A | 10/1996 | Graf |
| 5,562,738 A | 10/1996 | Boyd et al. |
| 5,571,109 A | 11/1996 | Bertagnoli |
| 5,609,635 A | 3/1997 | Michelson |
| 5,624,442 A | 4/1997 | Mellinger et al. |
| 5,645,599 A | 7/1997 | Samani |
| 5,653,763 A | 8/1997 | Errico et al. |
| 5,658,335 A | 8/1997 | Allen |
| 5,665,122 A | 9/1997 | Kambin |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,701 A | 10/1997 | Yuan et al. |
| 5,676,702 A | 10/1997 | Ratron |
| 5,683,391 A | 11/1997 | Boyd |
| 5,683,394 A | 11/1997 | Rinner |
| 5,683,464 A | 11/1997 | Wagner et al. |
| 5,683,465 A | 11/1997 | Shinn et al. |
| 5,702,450 A | 12/1997 | Bisserie |
| 5,725,527 A | 3/1998 | Biedermann et al. |
| 5,733,284 A | 3/1998 | Martin |
| 5,741,253 A | 4/1998 | Michelson |
| 5,755,797 A | 5/1998 | Baumgartner |
| 5,772,661 A | 6/1998 | Michelson |
| 5,776,199 A | 7/1998 | Michelson |
| 5,782,832 A | 7/1998 | Larsen et al. |
| 5,785,647 A | 7/1998 | Tompkins et al. |
| 5,797,909 A | 8/1998 | Michelson |
| 5,800,547 A | 9/1998 | Schafer et al. |
| 5,800,549 A | 9/1998 | Bao et al. |
| 5,800,550 A | 9/1998 | Sertich |
| 5,810,819 A | 9/1998 | Errico et al. |
| 5,810,820 A | 9/1998 | Santori et al. |
| 5,824,093 A | 10/1998 | Ray et al. |
| 5,824,094 A | 10/1998 | Serhan et al. |
| 5,827,328 A | 10/1998 | Buttermann |
| 5,836,960 A | 11/1998 | Kolesa et al. |
| 5,849,004 A | 12/1998 | Bramlet |
| 5,860,973 A | 1/1999 | Michelson |
| 5,861,041 A | 1/1999 | Tienboon |
| 5,863,293 A | 1/1999 | Richelsoph |
| 5,865,846 A | 2/1999 | Bryan et al. |
| 5,865,848 A | 2/1999 | Baker |
| 5,888,220 A | 3/1999 | Felt et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,928,243 A | 7/1999 | Guyer |
| 5,935,133 A | 8/1999 | Wagner et al. |
| 5,938,663 A | 8/1999 | Petreto |
| 5,951,555 A | 9/1999 | Rehak et al. |
| 5,961,518 A | 10/1999 | Errico et al. |
| 5,961,554 A | 10/1999 | Janson et al. |
| 5,964,769 A | 10/1999 | Wagner et al. |
| 5,976,186 A | 11/1999 | Bao et al. |
| 5,980,522 A | 11/1999 | Koros et al. |
| 5,984,967 A | 11/1999 | Zdeblick et al. |
| 5,989,250 A | 11/1999 | Wagner et al. |
| 5,989,290 A | 11/1999 | Biedermann et al. |
| 5,997,539 A | 12/1999 | Errico et al. |
| 6,001,130 A | 12/1999 | Bryan et al. |
| 6,017,344 A | 1/2000 | Errico et al. |
| 6,019,792 A | 2/2000 | Cauthen |
| 6,022,376 A | 2/2000 | Assell et al. |
| 6,030,389 A | 2/2000 | Wagner et al. |
| 6,039,763 A | 3/2000 | Shelokov |
| 6,045,552 A | 4/2000 | Zucherman et al. |
| 6,045,579 A | 4/2000 | Hochshuler et al. |
| 6,053,921 A | 4/2000 | Wagner et al. |
| 6,063,089 A | 5/2000 | Errico et al. |
| RE36,758 E | 6/2000 | Fitz |
| 6,080,193 A | 6/2000 | Hochshuler et al. |
| 6,093,205 A | 7/2000 | McLeod et al. |
| 6,096,038 A | 8/2000 | Michelson |
| 6,099,531 A | 8/2000 | Bonutti |
| 6,102,950 A * | 8/2000 | Vaccaro .......... A61F 2/447 606/247 |
| 6,106,526 A | 8/2000 | Harms et al. |
| 6,110,210 A | 8/2000 | Norton et al. |
| 6,113,637 A | 9/2000 | Gill et al. |
| 6,113,638 A | 9/2000 | Williams et al. |
| 6,123,707 A | 9/2000 | Wagner et al. |
| 6,126,689 A | 10/2000 | Brett |
| 6,132,430 A | 10/2000 | Wagner et al. |
| 6,132,464 A | 10/2000 | Martin |
| 6,132,465 A | 10/2000 | Ray et al. |
| 6,136,001 A | 10/2000 | Michelson |
| 6,136,031 A | 10/2000 | Middleton |

(56) References Cited

U.S. PATENT DOCUMENTS

| | | |
|---|---|---|
| 6,139,579 A | 10/2000 | Steffee et al. |
| 6,146,421 A | 11/2000 | Gordon et al. |
| 6,146,422 A | 11/2000 | Lawson |
| 6,156,067 A | 12/2000 | Bryan et al. |
| 6,159,244 A | 12/2000 | Suddaby |
| 6,162,252 A | 12/2000 | Kuras et al. |
| 6,165,218 A | 12/2000 | Husson et al. |
| 6,176,882 B1 | 1/2001 | Biedermann et al. |
| 6,179,873 B1 | 1/2001 | Zientek |
| 6,179,874 B1 | 1/2001 | Cauthen |
| 6,186,034 B1 | 2/2001 | Lamons |
| 6,187,048 B1 | 2/2001 | Milner et al. |
| 6,200,348 B1 | 3/2001 | Biedermann et al. |
| 6,206,924 B1 | 3/2001 | Timm |
| 6,214,049 B1 | 4/2001 | Gayer et al. |
| 6,214,050 B1 | 4/2001 | Huene |
| 6,217,579 B1 | 4/2001 | Koros |
| 6,228,118 B1 | 5/2001 | Gordon |
| 6,231,609 B1 | 5/2001 | Mehdizadeh |
| 6,241,730 B1 | 6/2001 | Alby |
| 6,264,656 B1 | 7/2001 | Michelson |
| 6,290,724 B1 | 9/2001 | Marino |
| 6,296,664 B1 | 10/2001 | Middleton |
| 6,315,797 B1 | 11/2001 | Middleton |
| 6,331,179 B1 | 12/2001 | Freid et al. |
| 6,348,071 B1 | 2/2002 | Steffee et al. |
| RE37,665 E | 4/2002 | Ralph et al. |
| 6,368,350 B1 | 4/2002 | Erickson |
| 6,368,351 B1 | 4/2002 | Glenn et al. |
| 6,371,990 B1 | 4/2002 | Ferree |
| 6,375,682 B1 | 4/2002 | Fleischmann et al. |
| 6,375,683 B1 | 4/2002 | Crozet et al. |
| 6,391,090 B1 | 5/2002 | Wagner et al. |
| 6,395,032 B1 | 5/2002 | Gauchet |
| 6,395,034 B1 | 5/2002 | Suddaby |
| 6,402,784 B1 | 6/2002 | Wardlaw |
| 6,402,785 B1 | 6/2002 | Zdeblick et al. |
| 6,409,766 B1 | 6/2002 | Brett |
| 6,413,259 B1 | 7/2002 | Lyons et al. |
| 6,416,515 B1 | 7/2002 | Wagner et al. |
| 6,419,703 B1 | 7/2002 | Fallin et al. |
| 6,419,704 B1 | 7/2002 | Ferree |
| 6,436,140 B1 | 8/2002 | Liu et al. |
| 6,440,168 B1 | 8/2002 | Cauthen |
| 6,442,814 B1 | 9/2002 | Landry et al. |
| 6,443,990 B1 | 9/2002 | Aebi et al. |
| 6,447,512 B1 | 9/2002 | Landry et al. |
| 6,447,544 B1 | 9/2002 | Michelson |
| 6,447,545 B1 | 9/2002 | Bagby |
| 6,447,546 B1 | 9/2002 | Bramlet et al. |
| 6,451,021 B1 | 9/2002 | Ralph et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,475,218 B2 | 11/2002 | Gournay et al. |
| 6,478,822 B1 | 11/2002 | Leroux et al. |
| 6,478,823 B1 | 11/2002 | Michelson |
| 6,482,207 B1 | 11/2002 | Errico |
| 6,482,234 B1 | 11/2002 | Weber et al. |
| 6,488,710 B2 | 12/2002 | Besselink |
| 6,491,724 B1 | 12/2002 | Ferree |
| 6,500,180 B1 | 12/2002 | Foley et al. |
| 6,500,205 B1 | 12/2002 | Michelson |
| 6,500,206 B1 | 12/2002 | Bryan |
| 6,520,996 B1 | 2/2003 | Manasas et al. |
| 6,524,312 B2 | 2/2003 | Landry et al. |
| 6,527,803 B1 | 3/2003 | Crozet et al. |
| 6,533,817 B1 | 3/2003 | Norton et al. |
| 6,533,818 B1 | 3/2003 | Weber et al. |
| 6,537,320 B1 | 3/2003 | Michelson |
| 6,540,748 B2 | 4/2003 | Lombardo |
| 6,558,423 B1 | 5/2003 | Michelson |
| 6,558,424 B2 | 5/2003 | Thalgott |
| 6,562,040 B1 | 5/2003 | Wagner et al. |
| 6,562,074 B2 | 5/2003 | Gerbec et al. |
| 6,565,566 B1 | 5/2003 | Wagner et al. |
| 6,565,605 B2 | 5/2003 | Goble et al. |
| 6,569,442 B2 | 5/2003 | Gan et al. |
| 6,572,653 B1 | 6/2003 | Simonson |
| 6,576,016 B1 | 6/2003 | Hochshuler et al. |
| 6,579,318 B2 | 6/2003 | Varga et al. |
| 6,579,319 B2 | 6/2003 | Goble et al. |
| 6,582,467 B1 | 6/2003 | Teitelbaum et al. |
| 6,592,624 B1 | 7/2003 | Fraser et al. |
| 6,595,992 B1 | 7/2003 | Wagner et al. |
| 6,595,998 B2 | 7/2003 | Johnson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,671 B2 | 9/2003 | Landry et al. |
| 6,626,904 B1 | 9/2003 | Jammet et al. |
| 6,626,905 B1 | 9/2003 | Schmeil et al. |
| 6,635,062 B2 | 10/2003 | Ray et al. |
| 6,641,614 B1 | 11/2003 | Wagner et al. |
| 6,648,893 B2 | 11/2003 | Dudasik |
| 6,648,915 B2 | 11/2003 | Sazy |
| 6,648,917 B2 | 11/2003 | Gerbec et al. |
| 6,666,870 B2 | 12/2003 | Dixon |
| 6,666,891 B2 | 12/2003 | Boehm et al. |
| 6,679,915 B1 | 1/2004 | Cauthen |
| 6,682,533 B1 | 1/2004 | Dinsdale et al. |
| 6,685,742 B1 | 2/2004 | Jackson |
| 6,692,495 B1 | 2/2004 | Zacouto |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,796 B2 | 4/2004 | Cohen et al. |
| 6,733,531 B1 | 5/2004 | Trieu |
| 6,736,850 B2 | 5/2004 | Davis |
| 6,743,257 B2 | 6/2004 | Castro |
| 6,758,861 B2 | 7/2004 | Ralph et al. |
| 6,767,367 B1 | 7/2004 | Michelson |
| 6,770,096 B2 | 8/2004 | Bolger et al. |
| 6,773,460 B2 | 8/2004 | Jackson |
| 6,800,092 B1 | 10/2004 | Williams et al. |
| 6,802,844 B2 | 10/2004 | Ferree |
| 6,811,567 B2 | 11/2004 | Reiley |
| 6,821,298 B1 | 11/2004 | Jackson |
| 6,852,129 B2 | 2/2005 | Gerbec et al. |
| 6,863,673 B2 | 3/2005 | Gerbec et al. |
| 6,893,464 B2 | 5/2005 | Kiester |
| 6,896,680 B2 | 5/2005 | Michelson |
| 6,902,580 B2 | 6/2005 | Fallin et al. |
| 6,923,830 B2 | 8/2005 | Michelson |
| 6,928,284 B2 | 8/2005 | Palat et al. |
| 6,936,070 B1 | 8/2005 | Muhanna |
| 6,936,071 B1 | 8/2005 | Marnay et al. |
| 6,953,477 B2 | 10/2005 | Berry |
| 6,962,606 B2 | 11/2005 | Michelson |
| 6,964,664 B2 | 11/2005 | Freid et al. |
| 6,966,929 B2 | 11/2005 | Mitchell |
| 6,966,930 B2 | 11/2005 | Arnin et al. |
| 6,974,478 B2 | 12/2005 | Reiley et al. |
| 6,981,975 B2 | 1/2006 | Michelson |
| 6,981,989 B1 | 1/2006 | Fleischmann et al. |
| 6,991,632 B2 | 1/2006 | Ritland |
| 6,994,727 B2 | 2/2006 | Khandkar et al. |
| 6,997,929 B2 | 2/2006 | Manzi et al. |
| 7,011,685 B2 | 3/2006 | Arnin et al. |
| 7,018,415 B1 | 3/2006 | McKay |
| 7,029,475 B2 | 4/2006 | Panjabi |
| 7,060,073 B2 | 6/2006 | Frey et al. |
| 7,060,100 B2 | 6/2006 | Ferree |
| 7,083,622 B2 | 8/2006 | Simonson |
| 7,083,649 B2 | 8/2006 | Zucherman et al. |
| 7,090,698 B2 | 8/2006 | Goble et al. |
| 7,101,398 B2 | 9/2006 | Dooris et al. |
| 7,112,206 B2 | 9/2006 | Michelson |
| 7,118,579 B2 | 10/2006 | Michelson |
| 7,118,580 B1 | 10/2006 | Beyersdorff et al. |
| 7,128,760 B2 | 10/2006 | Michelson |
| 7,147,664 B2 | 12/2006 | Louis et al. |
| 7,153,310 B2 | 12/2006 | Ralph et al. |

(56) References Cited

U.S. PATENT DOCUMENTS

| | | |
|---|---|---|
| 7,198,644 B2 | 4/2007 | Schultz et al. |
| 7,204,852 B2 | 4/2007 | Marnay et al. |
| 7,204,853 B2 | 4/2007 | Gordon et al. |
| 7,270,681 B2 | 9/2007 | Cauthen |
| 7,273,496 B2 | 9/2007 | Mitchell |
| 7,291,150 B2 | 11/2007 | Graf |
| 7,291,159 B2 | 11/2007 | Graf |
| 7,291,173 B2 | 11/2007 | Richelsoph et al. |
| 7,311,713 B2 | 12/2007 | Johnson et al. |
| 7,316,714 B2 | 1/2008 | Gordon et al. |
| 7,318,839 B2 | 1/2008 | Malberg et al. |
| 7,320,707 B2 | 1/2008 | Zucherman |
| 7,326,250 B2 | 2/2008 | Beaurain et al. |
| 7,338,525 B2 | 3/2008 | Ferree |
| 7,338,527 B2 | 3/2008 | Blatt et al. |
| 7,364,589 B2 | 4/2008 | Eisermann |
| 7,473,276 B2 | 1/2009 | Aebi et al. |
| 7,476,238 B2 | 1/2009 | Panjabi |
| 7,485,146 B1 | 2/2009 | Crook et al. |
| 7,517,359 B2 | 4/2009 | Drewry et al. |
| 7,547,309 B2 | 6/2009 | Bertagnoli et al. |
| 7,550,009 B2 | 6/2009 | Arnin et al. |
| 7,556,651 B2 | 7/2009 | Humphreys et al. |
| 7,575,580 B2 | 8/2009 | Lim et al. |
| 7,594,932 B2 | 9/2009 | Aferzon et al. |
| 7,615,068 B2 | 11/2009 | Timm et al. |
| 7,635,379 B2 | 12/2009 | Callahan et al. |
| 7,682,396 B2 | 3/2010 | Beaurain et al. |
| 7,699,875 B2 | 4/2010 | Timm et al. |
| 7,708,778 B2 | 5/2010 | Gordon et al. |
| 7,713,287 B2 | 5/2010 | Timm et al. |
| 7,713,288 B2 | 5/2010 | Timm et al. |
| 7,727,280 B2 | 6/2010 | McLuen |
| 7,753,958 B2 | 7/2010 | Gordon et al. |
| 7,771,479 B2 | 8/2010 | Humphreys et al. |
| 7,785,351 B2 | 8/2010 | Gordon et al. |
| 7,794,480 B2 | 9/2010 | Gordon et al. |
| 7,799,082 B2 | 9/2010 | Gordon et al. |
| 7,811,309 B2 | 10/2010 | Timm et al. |
| 7,819,801 B2 | 10/2010 | Miles et al. |
| 7,828,849 B2 | 11/2010 | Lim |
| 7,846,188 B2 | 12/2010 | Moskowitz et al. |
| 7,896,919 B2 | 3/2011 | Belliard et al. |
| 7,909,869 B2 | 3/2011 | Gordon et al. |
| 7,909,877 B2 | 3/2011 | Krueger et al. |
| 7,927,374 B2 | 4/2011 | Duggal et al. |
| 7,931,675 B2 | 4/2011 | Panjabi et al. |
| 7,942,905 B2 | 5/2011 | Lim et al. |
| 7,951,170 B2 | 5/2011 | Jackson |
| 7,959,677 B2 | 6/2011 | Landry et al. |
| 8,043,379 B2 | 10/2011 | Moumene et al. |
| 8,052,723 B2 | 11/2011 | Gordon et al. |
| 8,062,375 B2 | 11/2011 | Glerum et al. |
| 8,080,062 B2 | 12/2011 | Armstrong et al. |
| 8,105,382 B2 | 1/2012 | Olmos et al. |
| 8,114,092 B2 | 2/2012 | Altarac et al. |
| 8,118,869 B2 | 2/2012 | Gordon et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,128,700 B2 | 3/2012 | Delurio et al. |
| 8,147,550 B2 | 4/2012 | Gordon et al. |
| 8,157,844 B2 | 4/2012 | Gimbel et al. |
| 8,162,994 B2 | 4/2012 | Gimbel et al. |
| 8,172,903 B2 | 5/2012 | Gordon et al. |
| 8,182,514 B2 | 5/2012 | Gimbel et al. |
| 8,187,330 B2 | 5/2012 | Gimbel et al. |
| 8,257,440 B2 | 9/2012 | Gordon et al. |
| 8,257,443 B2 | 9/2012 | Kamran et al. |
| 8,267,965 B2 | 9/2012 | Gimbel et al. |
| 8,303,660 B1 | 11/2012 | Abdou |
| 8,313,528 B1 | 11/2012 | Wensel |
| 8,377,098 B2 | 2/2013 | Landry et al. |
| 8,388,687 B2 | 3/2013 | Gimbel et al. |
| 8,398,713 B2 | 3/2013 | Weiman |
| 8,414,652 B2 | 4/2013 | Moumene et al. |
| 8,435,298 B2 | 5/2013 | Weiman |
| 8,475,461 B2 | 7/2013 | Butler et al. |
| 8,486,148 B2 | 7/2013 | Butler et al. |
| 8,491,659 B2 | 7/2013 | Weiman |
| 8,512,407 B2 | 8/2013 | Butler et al. |
| 8,518,120 B2 | 8/2013 | Glerum et al. |
| 8,523,912 B2 | 9/2013 | Gimbel et al. |
| 8,545,563 B2 | 10/2013 | Brun et al. |
| 8,556,979 B2 | 10/2013 | Glerum et al. |
| 8,591,553 B2 | 11/2013 | Eisermann et al. |
| 8,597,358 B2 | 12/2013 | Landry et al. |
| 8,603,168 B2 | 12/2013 | Gordon et al. |
| 8,632,595 B2 | 1/2014 | Weiman |
| 8,647,386 B2 | 2/2014 | Gordon et al. |
| 8,679,183 B2 | 3/2014 | Glerum et al. |
| 8,685,098 B2 | 4/2014 | Glerum et al. |
| 8,709,086 B2 | 4/2014 | Glerum |
| 8,753,398 B2 | 6/2014 | Gordon et al. |
| 8,940,022 B2 | 1/2015 | Landry et al. |
| 8,940,051 B2 | 1/2015 | Gimbel et al. |
| 2001/0020476 A1 | 9/2001 | Gan et al. |
| 2001/0032020 A1 | 10/2001 | Besselink |
| 2002/0040243 A1 | 4/2002 | Attali et al. |
| 2002/0045945 A1 | 4/2002 | Liu et al. |
| 2002/0065557 A1 | 5/2002 | Goble et al. |
| 2002/0068977 A1 | 6/2002 | Jackson |
| 2002/0072801 A1 | 6/2002 | Michelson |
| 2002/0082701 A1 | 6/2002 | Zdeblick et al. |
| 2002/0091390 A1 | 7/2002 | Michelson |
| 2002/0095154 A1 | 7/2002 | Atkinson et al. |
| 2002/0123806 A1 | 9/2002 | Reiley |
| 2002/0128659 A1 | 9/2002 | Michelson |
| 2002/0128714 A1 | 9/2002 | Manasas et al. |
| 2002/0130112 A1 | 9/2002 | Manasas et al. |
| 2002/0138077 A1 | 9/2002 | Ferree |
| 2002/0143401 A1 | 10/2002 | Michelson |
| 2003/0028250 A1 | 2/2003 | Reiley et al. |
| 2003/0040802 A1 | 2/2003 | Errico |
| 2003/0055427 A1 | 3/2003 | Graf |
| 2003/0069643 A1 | 4/2003 | Ralph et al. |
| 2003/0074063 A1 | 4/2003 | Gerbec et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0135275 A1 | 7/2003 | Garcia et al. |
| 2003/0135277 A1 | 7/2003 | Bryan et al. |
| 2003/0139812 A1 | 7/2003 | Garcia et al. |
| 2003/0149483 A1 | 8/2003 | Michelson |
| 2003/0176923 A1 | 9/2003 | Keller et al. |
| 2003/0187436 A1 | 10/2003 | Bolger et al. |
| 2003/0191470 A1 | 10/2003 | Ritland |
| 2003/0204259 A1 | 10/2003 | Goble et al. |
| 2003/0204260 A1 | 10/2003 | Ferree |
| 2003/0220643 A1 | 11/2003 | Ferree |
| 2003/0225409 A1 | 12/2003 | Freid et al. |
| 2003/0233145 A1 | 12/2003 | Landry et al. |
| 2004/0006391 A1 | 1/2004 | Reiley |
| 2004/0010312 A1 | 1/2004 | Enayati |
| 2004/0019353 A1 | 1/2004 | Freid et al. |
| 2004/0030387 A1 | 2/2004 | Landry et al. |
| 2004/0030389 A1 | 2/2004 | Ferree |
| 2004/0039448 A1 | 2/2004 | Pisharodi |
| 2004/0044411 A1 | 3/2004 | Suddaby |
| 2004/0049190 A1 | 3/2004 | Biedermann et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |

(56) References Cited

U.S. PATENT DOCUMENTS

| | | |
|---|---|---|
| 2004/0049280 A1 | 3/2004 | Cauthen |
| 2004/0049281 A1 | 3/2004 | Reiley |
| 2004/0064136 A1 | 4/2004 | Papineau et al. |
| 2004/0087947 A1 | 5/2004 | Lim et al. |
| 2004/0093083 A1 | 5/2004 | Branch et al. |
| 2004/0102774 A1 | 5/2004 | Trieu |
| 2004/0106997 A1 | 6/2004 | Lieberson |
| 2004/0117020 A1 | 6/2004 | Frey et al. |
| 2004/0127989 A1 | 7/2004 | Dooris et al. |
| 2004/0133278 A1 | 7/2004 | Marino et al. |
| 2004/0133281 A1 | 7/2004 | Khandkar et al. |
| 2004/0138662 A1 | 7/2004 | Landry et al. |
| 2004/0138749 A1 | 7/2004 | Zucherman |
| 2004/0143265 A1 | 7/2004 | Landry et al. |
| 2004/0143332 A1 | 7/2004 | Krueger et al. |
| 2004/0147928 A1 | 7/2004 | Landry et al. |
| 2004/0153065 A1 | 8/2004 | Lim |
| 2004/0167626 A1 | 8/2004 | Geremakis et al. |
| 2004/0181223 A1 | 9/2004 | Ritland |
| 2004/0181284 A1 | 9/2004 | Simonson |
| 2004/0220567 A1 | 11/2004 | Eisermann et al. |
| 2004/0236327 A1 | 11/2004 | Paul et al. |
| 2004/0236329 A1 | 11/2004 | Panjabi |
| 2004/0243240 A1 | 12/2004 | Beaurain et al. |
| 2004/0254643 A1 | 12/2004 | Jackson |
| 2004/0254644 A1 | 12/2004 | Taylor |
| 2004/0267364 A1 | 12/2004 | Carli et al. |
| 2004/0267369 A1 | 12/2004 | Lyons et al. |
| 2005/0010295 A1 | 1/2005 | Michelson |
| 2005/0015146 A1 | 1/2005 | Louis et al. |
| 2005/0015149 A1 | 1/2005 | Michelson |
| 2005/0021144 A1 | 1/2005 | Malberg et al. |
| 2005/0027361 A1 | 2/2005 | Reiley |
| 2005/0027362 A1 | 2/2005 | Williams et al. |
| 2005/0033431 A1 | 2/2005 | Gordon et al. |
| 2005/0033432 A1 | 2/2005 | Gordon et al. |
| 2005/0033437 A1 | 2/2005 | Bao et al. |
| 2005/0033439 A1 | 2/2005 | Gordon et al. |
| 2005/0043800 A1 | 2/2005 | Paul et al. |
| 2005/0060034 A1 | 3/2005 | Berry |
| 2005/0085815 A1 | 4/2005 | Harms et al. |
| 2005/0096745 A1 | 5/2005 | Andre et al. |
| 2005/0107881 A1 | 5/2005 | Neville et al. |
| 2005/0113927 A1 | 5/2005 | Malek |
| 2005/0124991 A1 | 6/2005 | Jahng |
| 2005/0125061 A1 | 6/2005 | Zucherman et al. |
| 2005/0125062 A1 | 6/2005 | Biedermann et al. |
| 2005/0131406 A1 | 6/2005 | Reiley |
| 2005/0131408 A1 | 6/2005 | Sicvol et al. |
| 2005/0143818 A1 | 6/2005 | Yuan et al. |
| 2005/0149020 A1 | 7/2005 | Jahng |
| 2005/0149023 A1 | 7/2005 | Ritland |
| 2005/0154461 A1 | 7/2005 | Humphreys et al. |
| 2005/0154462 A1 | 7/2005 | Zucherman et al. |
| 2005/0154465 A1 | 7/2005 | Hodges et al. |
| 2005/0154466 A1 | 7/2005 | Humphreys et al. |
| 2005/0159818 A1 | 7/2005 | Blain |
| 2005/0171543 A1 | 8/2005 | Timm et al. |
| 2005/0171608 A1 | 8/2005 | Peterman et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0209697 A1 | 9/2005 | Paponneau et al. |
| 2005/0209698 A1 | 9/2005 | Gordon et al. |
| 2005/0222569 A1 | 10/2005 | Panjabi |
| 2005/0228500 A1 | 10/2005 | Kim et al. |
| 2005/0245930 A1 | 11/2005 | Timm et al. |
| 2005/0251261 A1 | 11/2005 | Peterman |
| 2005/0256578 A1 | 11/2005 | Blatt et al. |
| 2005/0261771 A1 | 11/2005 | Paul et al. |
| 2005/0273167 A1 | 12/2005 | Triplett et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288670 A1 | 12/2005 | Panjabi et al. |
| 2006/0009768 A1 | 1/2006 | Ritland |
| 2006/0009850 A1 | 1/2006 | Frigg et al. |
| 2006/0015100 A1 | 1/2006 | Panjabi et al. |
| 2006/0036240 A1 | 2/2006 | Colleran |
| 2006/0036245 A1 | 2/2006 | Stern |
| 2006/0084986 A1 | 4/2006 | Grinberg et al. |
| 2006/0084988 A1 | 4/2006 | Kim |
| 2006/0089717 A1 | 4/2006 | Krishna et al. |
| 2006/0095132 A1 | 5/2006 | Kirschman |
| 2006/0122701 A1 | 6/2006 | Kiester |
| 2006/0129244 A1 | 6/2006 | Ensign |
| 2006/0142759 A1 | 6/2006 | Arnin et al. |
| 2006/0149228 A1 | 7/2006 | Schlapfer et al. |
| 2006/0149229 A1 | 7/2006 | Kwak et al. |
| 2006/0149278 A1 | 7/2006 | Abdou |
| 2006/0149372 A1 | 7/2006 | Paxson et al. |
| 2006/0149383 A1 | 7/2006 | Arnin et al. |
| 2006/0149385 A1 | 7/2006 | McKay |
| 2006/0155377 A1 | 7/2006 | Beaurain et al. |
| 2006/0167547 A1 | 7/2006 | Suddaby |
| 2006/0178745 A1 | 8/2006 | Bartish et al. |
| 2006/0178746 A1 | 8/2006 | Bartish et al. |
| 2006/0189983 A1 | 8/2006 | Fallin et al. |
| 2006/0195114 A1 | 8/2006 | Bertagnoli |
| 2006/0195191 A1 | 8/2006 | Sweeney et al. |
| 2006/0195192 A1 | 8/2006 | Gordon et al. |
| 2006/0217712 A1 | 9/2006 | Mueller et al. |
| 2006/0229729 A1 | 10/2006 | Gordon |
| 2006/0235426 A1 | 10/2006 | Lim et al. |
| 2006/0241642 A1 | 10/2006 | Arnin et al. |
| 2006/0241769 A1 | 10/2006 | Gordon et al. |
| 2006/0241770 A1 | 10/2006 | Rhoda et al. |
| 2006/0241771 A1 | 10/2006 | Gordon et al. |
| 2006/0247635 A1 | 11/2006 | Gordon et al. |
| 2006/0247779 A1 | 11/2006 | Gordon et al. |
| 2006/0260483 A1 | 11/2006 | Hartmann et al. |
| 2006/0264937 A1 | 11/2006 | White |
| 2006/0265068 A1 | 11/2006 | Schwab |
| 2006/0265074 A1 | 11/2006 | Krishna |
| 2006/0265077 A1 | 11/2006 | Zwirkoski |
| 2007/0010886 A1 | 1/2007 | Banick |
| 2007/0032871 A1* | 2/2007 | Michelson ............ A61F 2/4455 623/17.11 |
| 2007/0073405 A1 | 3/2007 | Verhulst et al. |
| 2007/0073406 A1 | 3/2007 | Gordon et al. |
| 2007/0093828 A1 | 4/2007 | Abdou |
| 2007/0093846 A1 | 4/2007 | Frigg et al. |
| 2007/0162137 A1 | 7/2007 | Kloss et al. |
| 2007/0213720 A1 | 9/2007 | Gordon et al. |
| 2007/0213737 A1 | 9/2007 | Schermerhorn et al. |
| 2007/0213821 A1 | 9/2007 | Kwak et al. |
| 2007/0225814 A1 | 9/2007 | Atkinson |
| 2007/0239279 A1 | 10/2007 | Francis |
| 2007/0270814 A1 | 11/2007 | Lim et al. |
| 2007/0270838 A1 | 11/2007 | Bruneau et al. |
| 2007/0270972 A1 | 11/2007 | Gordon et al. |
| 2007/0288094 A1 | 12/2007 | Krishna et al. |
| 2008/0015702 A1 | 1/2008 | Lakin et al. |
| 2008/0021285 A1 | 1/2008 | Drzyzga et al. |
| 2008/0027547 A1 | 1/2008 | Yu et al. |
| 2008/0033562 A1 | 2/2008 | Krishna |
| 2008/0065079 A1 | 3/2008 | Bruneau et al. |
| 2008/0133013 A1 | 6/2008 | Duggal et al. |
| 2008/0161853 A1 | 7/2008 | Arnold et al. |
| 2008/0177310 A1 | 7/2008 | Reiley |
| 2008/0183204 A1 | 7/2008 | Greenhalgh et al. |
| 2008/0234732 A1 | 9/2008 | Landry et al. |
| 2008/0234740 A1 | 9/2008 | Landry et al. |

(56) References Cited

U.S. PATENT DOCUMENTS

| | | | |
|---|---|---|---|
| 2008/0234741 A1 | 9/2008 | Landry et al. | |
| 2008/0234764 A1 | 9/2008 | Landry et al. | |
| 2008/0234823 A1 | 9/2008 | Landry et al. | |
| 2008/0249628 A1 | 10/2008 | Altarac et al. | |
| 2008/0300685 A1 | 12/2008 | Carls et al. | |
| 2008/0306488 A1 | 12/2008 | Altarac et al. | |
| 2008/0306489 A1 | 12/2008 | Altarac et al. | |
| 2008/0306557 A1 | 12/2008 | Altarac et al. | |
| 2008/0312692 A1 | 12/2008 | Brennan et al. | |
| 2009/0005817 A1 | 1/2009 | Friedrich et al. | |
| 2009/0076549 A1 | 3/2009 | Lim et al. | |
| 2009/0076616 A1* | 3/2009 | Duggal | A61B 17/1604 623/17.16 |
| 2009/0093846 A1 | 4/2009 | Hestad | |
| 2009/0105757 A1 | 4/2009 | Gimbel et al. | |
| 2009/0105758 A1 | 4/2009 | Gimbel et al. | |
| 2009/0105759 A1 | 4/2009 | Gimbel et al. | |
| 2009/0105764 A1 | 4/2009 | Jackson | |
| 2009/0105820 A1 | 4/2009 | Jackson | |
| 2009/0105827 A1 | 4/2009 | Gimbel et al. | |
| 2009/0105828 A1 | 4/2009 | Gimbel et al. | |
| 2009/0105829 A1 | 4/2009 | Gimbel et al. | |
| 2009/0143862 A1 | 6/2009 | Trieu | |
| 2009/0177196 A1 | 7/2009 | Zlock et al. | |
| 2009/0270870 A1 | 10/2009 | Zubok et al. | |
| 2010/0030336 A1 | 2/2010 | Cope | |
| 2010/0082109 A1 | 4/2010 | Greenhalgh et al. | |
| 2010/0100138 A1 | 4/2010 | Reynolds et al. | |
| 2010/0174317 A1 | 7/2010 | Timm et al. | |
| 2010/0185289 A1 | 7/2010 | Kirwan et al. | |
| 2010/0191336 A1 | 7/2010 | Greenhalgh | |
| 2010/0204795 A1 | 8/2010 | Greenhalgh | |
| 2010/0211176 A1 | 8/2010 | Greenhalgh | |
| 2010/0222819 A1 | 9/2010 | Timm et al. | |
| 2010/0222884 A1 | 9/2010 | Greenhalgh | |
| 2010/0292796 A1 | 11/2010 | Greenhalgh et al. | |
| 2010/0298941 A1 | 11/2010 | Hes et al. | |
| 2010/0331985 A1 | 12/2010 | Gordon et al. | |
| 2011/0015742 A1 | 1/2011 | Hong | |
| 2011/0172774 A1* | 7/2011 | Varela | A61F 2/447 623/17.16 |
| 2011/0178599 A1 | 7/2011 | Brett | |
| 2011/0184522 A1* | 7/2011 | Melkent | A61F 2/4611 623/17.16 |
| 2011/0196428 A1 | 8/2011 | Panjabi et al. | |
| 2011/0208311 A1 | 8/2011 | Janowski | |
| 2011/0230971 A1 | 9/2011 | Donner et al. | |
| 2011/0319997 A1 | 12/2011 | Glerum et al. | |
| 2012/0035729 A1 | 2/2012 | Glerum et al. | |
| 2012/0143254 A1 | 6/2012 | Gimbel et al. | |
| 2012/0245689 A1 | 9/2012 | Gimbel et al. | |
| 2012/0265309 A1 | 10/2012 | Glerum et al. | |
| 2012/0310349 A1 | 12/2012 | Gordon et al. | |
| 2013/0023994 A1 | 1/2013 | Glerum | |
| 2013/0158667 A1 | 6/2013 | Tabor et al. | |
| 2013/0158669 A1 | 6/2013 | Sungarian et al. | |
| 2013/0245769 A1 | 9/2013 | Gimbel et al. | |
| 2014/0067071 A1 | 3/2014 | Weiman et al. | |

* cited by examiner

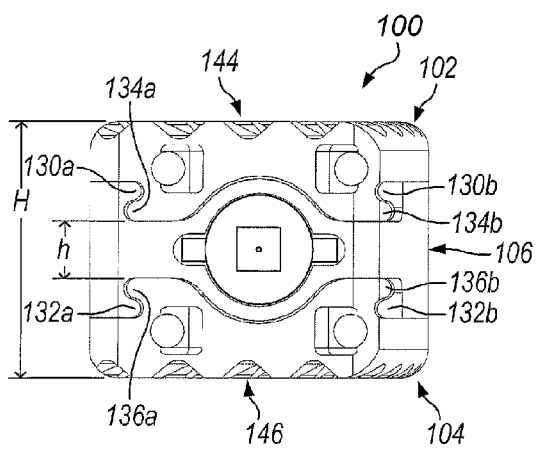
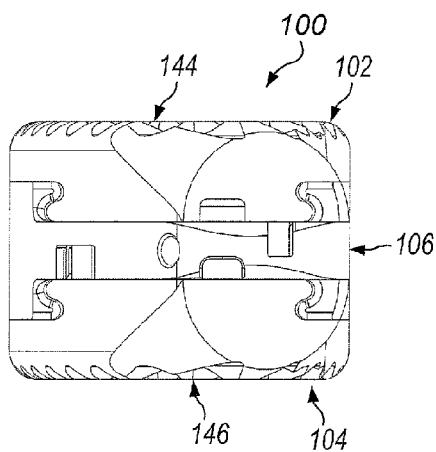
FIG. 1C        FIG. 1D
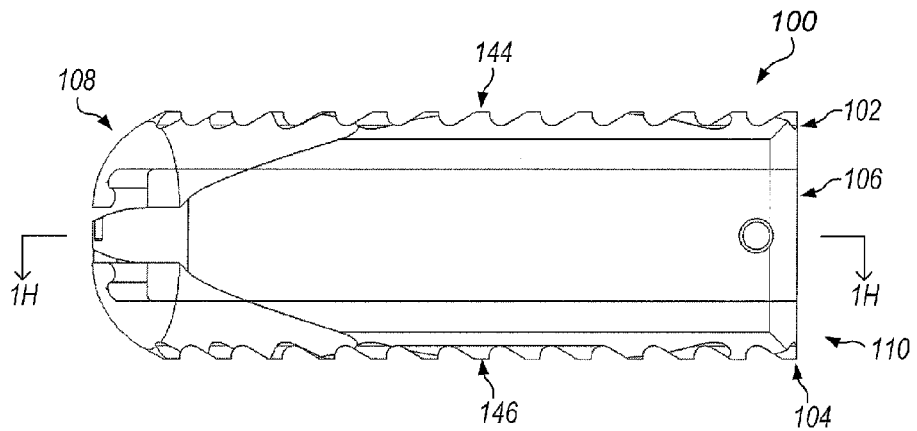
FIG. 1B
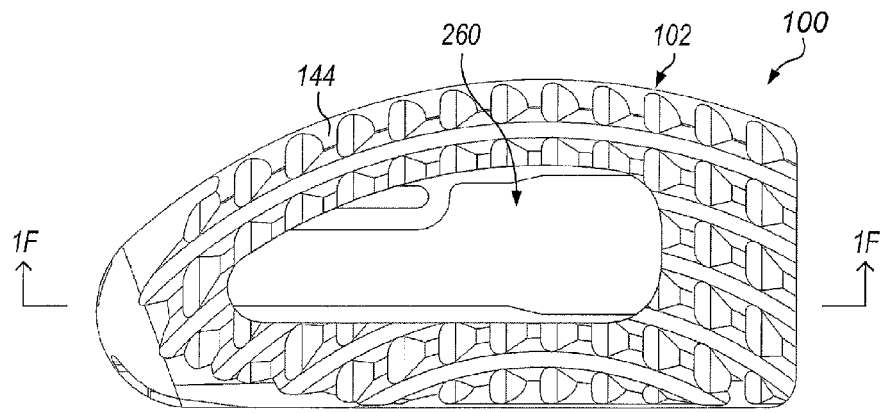
FIG. 1E

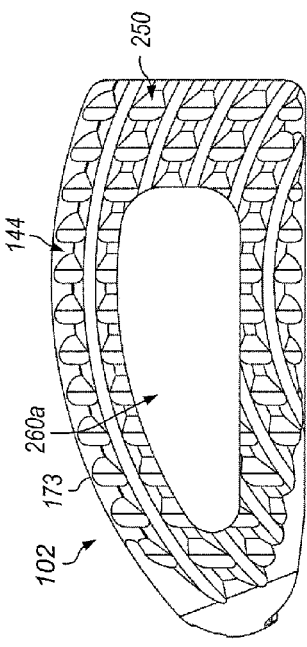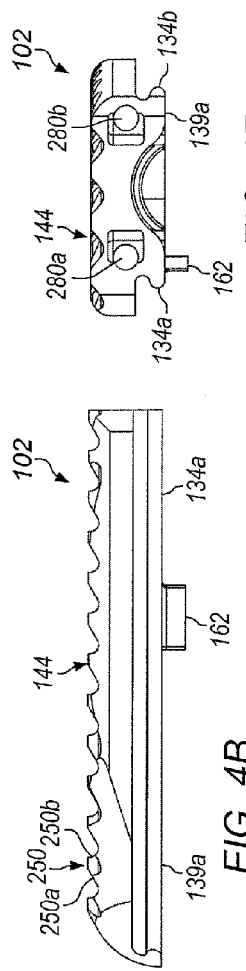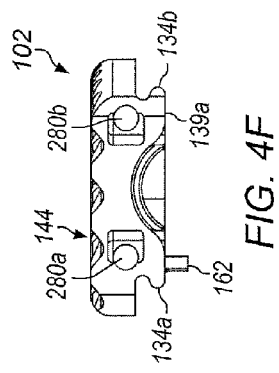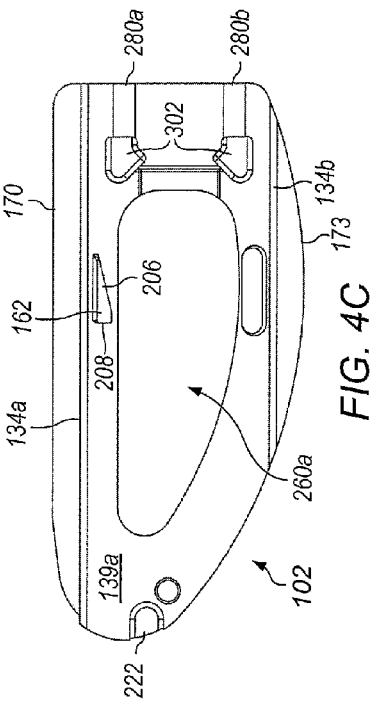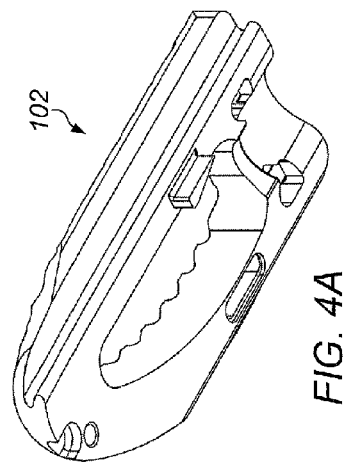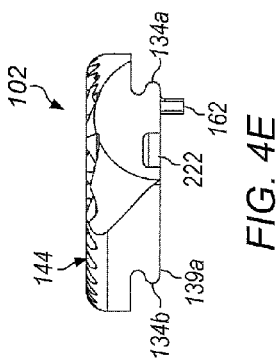

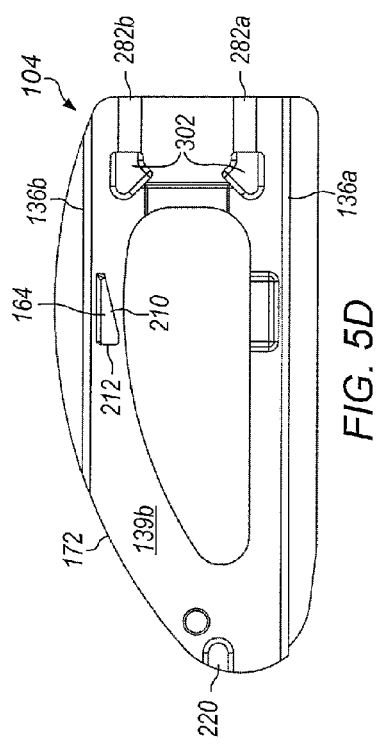
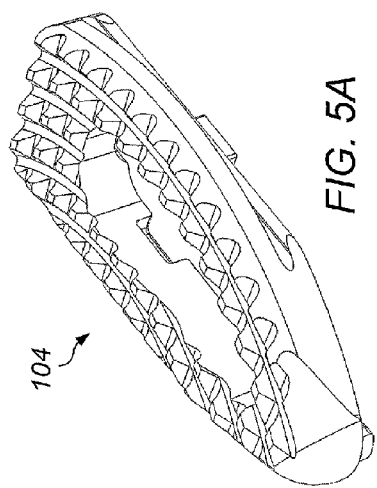
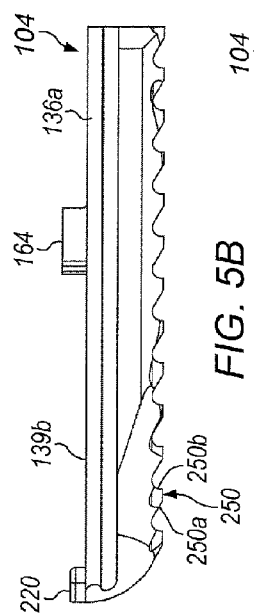
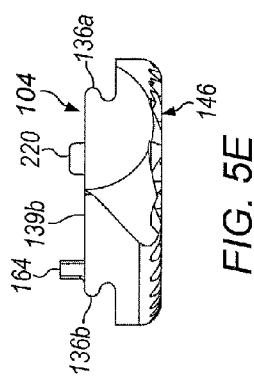
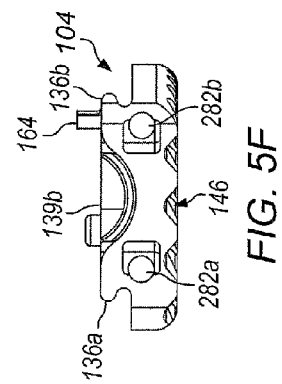
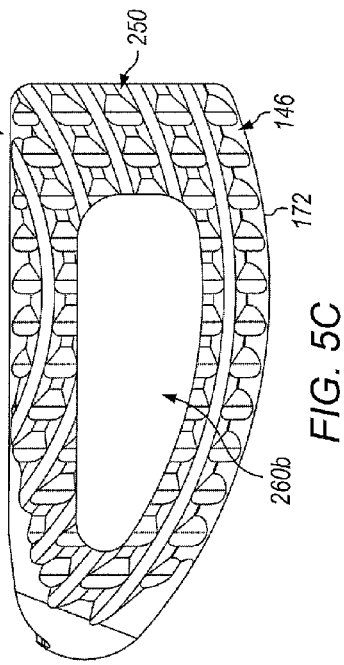
FIG. 5A
FIG. 5B
FIG. 5C
FIG. 5D
FIG. 5E
FIG. 5F

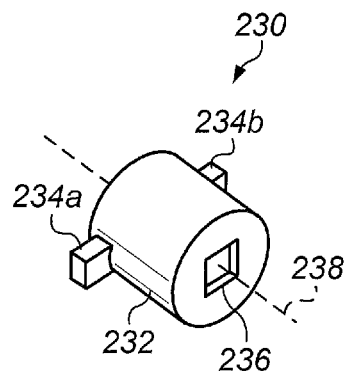 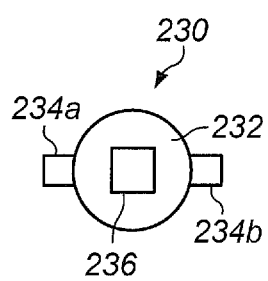 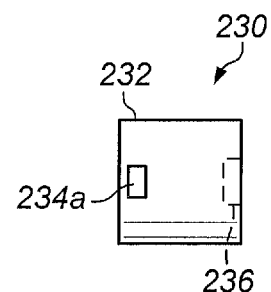
*FIG. 6A*          *FIG. 6B*          *FIG. 6C*
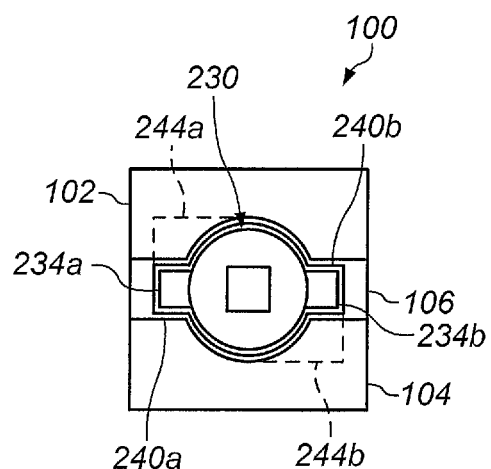 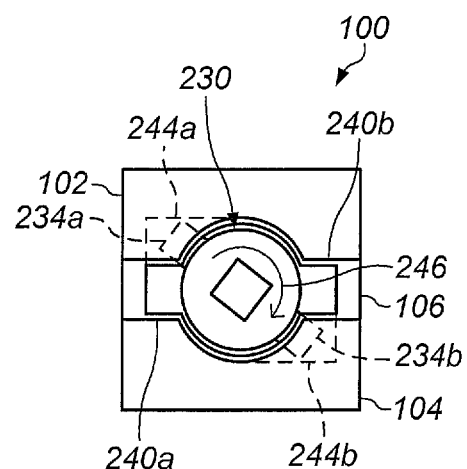
*FIG. 7A*          *FIG. 7B*

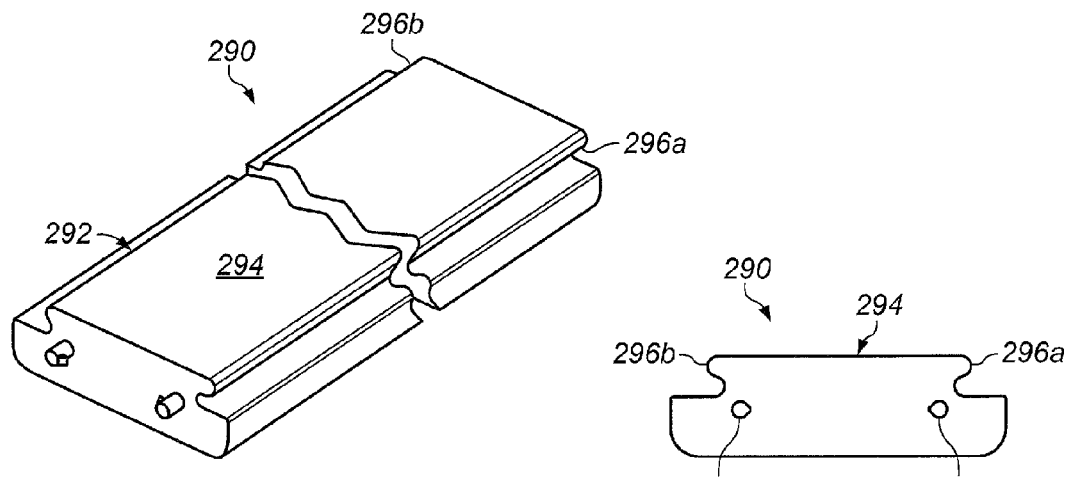
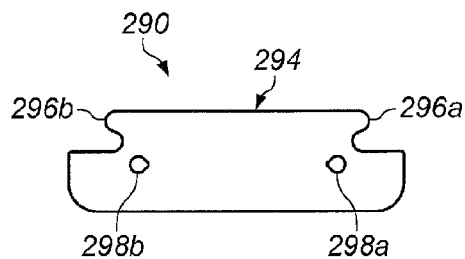
FIG. 8A
FIG. 8C
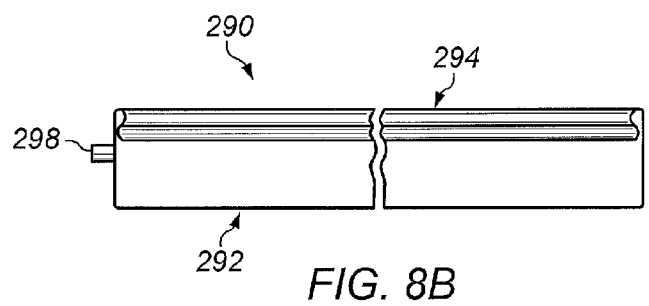
FIG. 8B
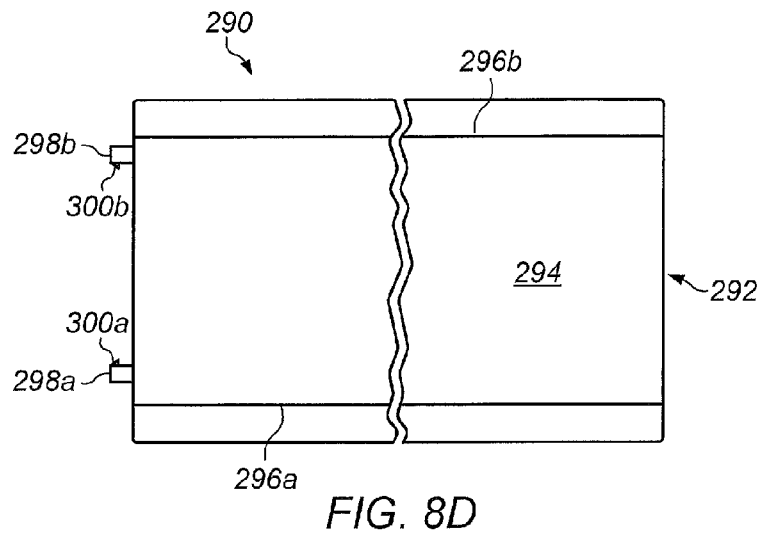
FIG. 8D

EXPANDABLE INTERBODY DEVICE SYSTEM AND METHOD

PRIORITY CLAIM

This application claims priority to U.S. Provisional Patent Application No. 61/561,037 entitled "EXPANDABLE INTERBODY DEVICE SYSTEM AND METHOD" filed on Nov. 17, 2011, which is incorporated by reference herein.

BACKGROUND

1. Field of the Invention

The present invention generally relates to spinal implants. More specifically, embodiments of the invention relate to expandable intervertebral implants for insertion into an intervertebral space between adjacent vertebrae of a human spine.

2. Description of Related Art

The human spine is a complex mechanical structure including alternating bony vertebrae and fibrocartilaginous discs that are connected by strong ligaments and supported by musculature that extends from the skull to the pelvis and provides axial support to the body. The intervertebral discs provide mechanical cushion between adjacent vertebral segments of the spinal column and include three basic components: the nucleus pulposus, the annulus fibrosis, and two vertebral end plates. The end plates are made of thin cartilage overlying a thin layer of hard cortical bone that attaches to the spongy, cancellous bone of the vertebral body. The annulus fibrosis forms the disc's perimeter and is a tough outer ring that binds adjacent vertebrae together. The vertebrae generally include a vertebral foramen bounded by the anterior vertebral body and the neural arch, which consists of two pedicles and two laminae that are united posteriorly. The spinous and transverse processes protrude from the neural arch. The superior and inferior articular facets lie at the root of the transverse process.

The human spine is highly flexible, capable of a high degree of curvature and twist in nearly every direction. Genetic or developmental irregularities, trauma, chronic stress, and degenerative wear, however, can result in spinal pathologies for which surgical intervention may be necessary. A disc may become damaged or diseased, reducing intervertebral separation. Reduction of the intervertebral separation may reduce a height of the disc nucleus, which may cause the annulus to buckle in areas where the laminated plies are loosely bonded. As the overlapping laminated plies of the annulus begin to buckle and separate, circumferential or radial annular tears may occur. Such disruption to the natural intervertebral separation may produce pain, which may be alleviated by removal of the disc and subsequently maintaining the natural separation of the vertebrae. In cases of chronic back pain resulting from a degenerated or herniated disc, removal of the disc becomes medically necessary.

In some instances, a damaged disc may be replaced with a disc prosthesis intended to duplicate the dynamic function of a natural spinal disc. In other cases, it may be desirable to fuse adjacent vertebrae of a human spine together after removal of a disc. This procedure is generally referred to as "intervertebral fusion" or "interbody fusion." Intervertebral fusion has been accomplished with a variety of techniques and instruments. In some instances intervertebral fusion has been accomplished by placing structural bone or interbody fusion cage implants filled with bone graft material (e.g., morselized bone) within an intervertebral space where the spinal disc once resided. Fusion cage implants have been generally successful in promoting fusion and maintaining suitable disc height. Insertion of fusion cage implants, however, may be difficult. For example, fusion cages inserted from a posterior approach are generally limited in size by the space between the nerve roots which the implant is moved through during insertion. Moreover, as the distance between vertebral end plates is reduced, the height of the intervertebral space is reduced, thereby limited the size of implants introduced into the space, and often requiring distraction (e.g., spreading of the vertebrae) to achieve a suitable separation of the vertebrae. To address these concerns, some implant designs include expandable implants. Expandable implants may include an undeployed/contracted configuration during insertion into the intervertebral space and may be expanded once inserted into the intervertebral space. Expansion may provide an expanded height to maintain a suitable separation of the vertebrae. Ideally, such expandable implant assemblies that are expanded within the intervertebral space may reduce potential trauma to the nerve roots and yet still allow restoration of disc space height. Unfortunately, the expandable implants may increase design complexity, may increase the complexity during implantation, may be unstable, or the like.

Accordingly, there is a desire to provide an expandable implant technique that provides a simple and reliable solution for intervertebral fusion.

SUMMARY

Various embodiments of spinal implant systems and related apparatus, and methods of operating the same are described. In one embodiment, provided is an intervertebral implant to be implanted within an intervertebral space between endplates of adjacent vertebra during use. The implant includes an upper member having an inferior surface including an upper guide track and a superior surface to contact an endplate of an upper one of the adjacent vertebra during use, a lower member having a superior surface including a lower guide track and an inferior surface to contact an endplate of a lower one of the adjacent vertebra during use, and an insert having a superior surface including an upper guide rail to engage the upper guide track during use and an inferior surface including a lower guide rail to engage the lower guide track during use. Engagement of the upper and lower guide rails with the upper and lower guide tracks, respectively, guides insertion of the insert between the upper and lower members during use, and insertion of the insert between the upper and lower members facilitates expansion of the intervertebral implant.

In another embodiment, provided is an intervertebral implant to be implanted within an intervertebral space between endplates of adjacent vertebra during use. The implant includes a first member having an interior surface including a first guide track, and an exterior surface to contact an endplate of a first of the adjacent vertebra during use, a second member including an interior surface comprising a second guide track and an exterior surface to contact an endplate of a second of the adjacent vertebra during use, and an insert including a first exterior surface including a first guide rail to engage the first guide track during use and a second exterior surface including a second guide rail to engage the second guide track during use. Engagement of the first and second guide rails with the first and second guide tracks, respectively, guides insertion of the insert between the first and second members during use, and insertion of the insert between the first and second members facilitates expansion of the intervertebral implant.

In another embodiment, provided is an intervertebral implant. The implant includes a first member to contact an endplate of a first vertebra during use, a second member to contact an endplate of a second vertebra during use, and an insert to be inserted between the first and second members to maintain the first and second members in an expanded position during use. The insert includes a longitudinally oriented guide insertion of the insert between the first and second member.

In another embodiment, provided is a method of implanting an intervertebral implant within an intervertebral space between endplates of adjacent vertebra. The method including inserting an upper member into the intervertebral space such that a superior surface of the upper member contacts an endplate of an upper one of the adjacent vertebra, wherein the upper member includes an inferior surface including an upper guide track, inserting a lower member into the intervertebral space such that an inferior surface of the lower member contacts an endplate of a lower one of the adjacent vertebra, wherein the lower member includes a superior surface including a lower guide track, inserting, between the upper and lower members, an insert including a superior surface including an upper guide rail and an inferior surface including a lower guide rail, where the upper guide rail engages the upper guide track and the lower guide rail engages the lower guide track. Engagement of the upper and lower guide rails with the upper and lower guide tracks, respectively, guides insertion of the insert between the upper and lower members, and wherein insertion of the insert between the upper and lower members facilitates expansion of the intervertebral implant.

In another embodiment, provided is a method of implanting an intervertebral implant within an intervertebral space between endplates of adjacent vertebra. The method includes inserting a first member into the intervertebral space such that an exterior surface of the first member contacts an endplate of a first of the adjacent vertebra, wherein the first member includes an interior surface including a first guide track, inserting a second member into the intervertebral space such that an exterior surface of the second member contacts an endplate of a second of the adjacent vertebra, wherein the second member includes an interior surface including a second guide track, inserting, between the first and second members, an insert including a first exterior surface including a first guide rail and a second exterior surface including a second guide rail, where the first guide rail engages the second guide track. Engagement of the first and second guide rails with the first and second guide tracks, respectively, guides insertion of the insert between the first and second members, and wherein insertion of the insert between the first and second members facilitates expansion of the intervertebral implant.

In another embodiment, provided is a method that includes inserting a first member between adjacent vertebra, wherein the first member contacts an endplate of a first of the adjacent vertebra during use, inserting a second member between the adjacent vertebra, wherein the second member contacts an endplate of a second of the adjacent vertebra during use, and inserting an insert between the first and second members to maintain the first and second members in an expanded position during use. The insert includes a longitudinally oriented guide insertion of the insert between the first and second member.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 1B, 1C, 1D and 1E illustrate a left-side view, a back/trailing-end view, a front/leading-end view, and a top view, respectively, of implant in accordance with one or more embodiments of the present technique.

FIGS. 4A, 4B, 4C, 4D, 4E and 4F depict a perspective view, a side view, a bottom view, a top view, a nose/leading-end view and a rear/trailing-end view, respectively of upper member 102 in accordance with one or more embodiments of the present technique.

FIGS. 5A, 5B, 5C, 5D, 5E and 5F depict a lower-perspective view, a side view, a bottom view, a top view, a nose/leading-end view, and a rear/trailing-end view, respectively of lower member 104 in accordance with one or more embodiments of the present technique.

FIGS. 6A, 6B and 6C illustrate a perspective view, a rear-end view and a side view, respectively, of a rotating locking member, in accordance with one or more embodiments of the present technique.

FIGS. 7A and 7B illustrate actuation of the locking member within the implant, in accordance with one or more embodiments of the present technique.

FIGS. 8A, 8B, 8C and 8D illustrate a perspective view, a side view, an end view, and a top view of a guide instrument, in accordance with one or more embodiments of the present technique.

Figure 1A:
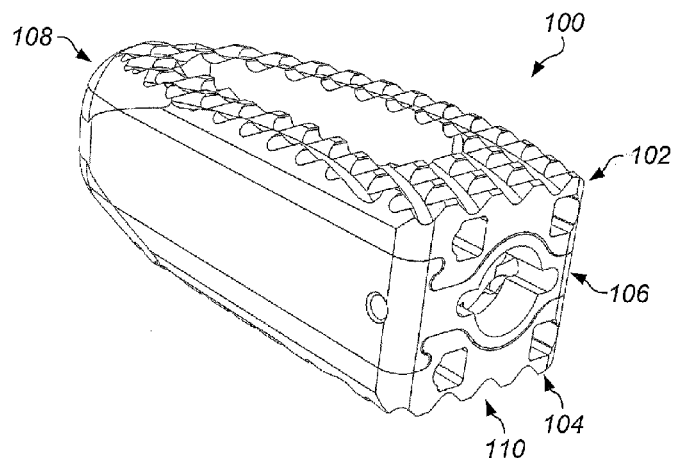
FIG. 1A illustrates a perspective view of an expandable implant system in accordance with one or more embodiments of the present technique.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DEFINITIONS

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

As discussed in more detail below, certain embodiments of the present technique include a systems and method for providing an intervertebral implant. In some embodiments, the intervertebral implant includes an expandable device that is disposed within an intervertebral space located between adjacent vertebrae of a human spine. In certain embodiments, the implant includes a spinal fusion implant that facilitates fusion of the adjacent vertebrae. In some embodiments, the implant includes several components, including an upper member, a lower member, and an insert. The components are provided in a sandwiched configuration, having the insert disposed between the upper and lower members. In certain embodiments, the upper and lower members are disposed within an intervertebral space and, the insert is advanced/inserted between the upper and lower members to distract the members relative to one another, thereby expanding the implant. In some embodiments, the upper and lower members are disposed adjacent the upper and lower vertebrae, respectively, such that expansion of the implant causes the upper and lower members to engage and distract the adjacent vertebrae.

In certain embodiments, advancement of the insert is facilitated by guide rails/tracks provided on the upper and lower members, the insert, and related instrumentation. In some embodiments, guides (e.g., rails/tracks) are provided on an inward facing (e.g., interior) surface of the first and second members, and complementary guides (e.g., complementary tracks/rails) are provided on the outward facing (e.g., exterior surface of the insert). In certain embodiments, the rails/tracks run longitudinally (e.g., substantially parallel to the direction of insertion) along lengths of the members and the insert to guide longitudinal advancement of the insert between the interior surfaces of the upper and lower members. In some embodiments, the rails/tracks may include one or more locking features that facilitate retention of the insert between the upper and lower members, thereby inhibiting back-out of the insert from between the members.

In certain embodiments, instrumentation facilitates expansion/distraction of the upper and lower members and/or to guide advancement of the insert between the upper and lower members. In some embodiments, instrument guide members engage trailing ends of the upper and lower members. In certain embodiments, the instrument guide members are used to insert the upper and lower members into the intervertebral space, and once the members have been inserted into the intervertebral space, the instrument guide members are spread apart to provide a distraction force that biases the upper and lower members away from one another into an expanded/distracted position. In certain embodiments, the distraction force is provided simultaneously with the advancement of the insert. In some embodiments, the distraction force provides for distraction of the upper and lower member of a sufficient amount to receive the insert between the members without any significant additional distraction. In certain embodiments, the distraction force is combined with other distraction forces generated as the insert is advanced/wedged between the upper and lower members, thereby providing a resulting distraction force that distracts the upper and lower members and causes distraction of the upper and lower member of a sufficient amount to receive the insert between the members. In some embodiments, all or substantially all the distraction force is generated as the insert is advanced/wedged between the upper and lower members.

Figure 1F:
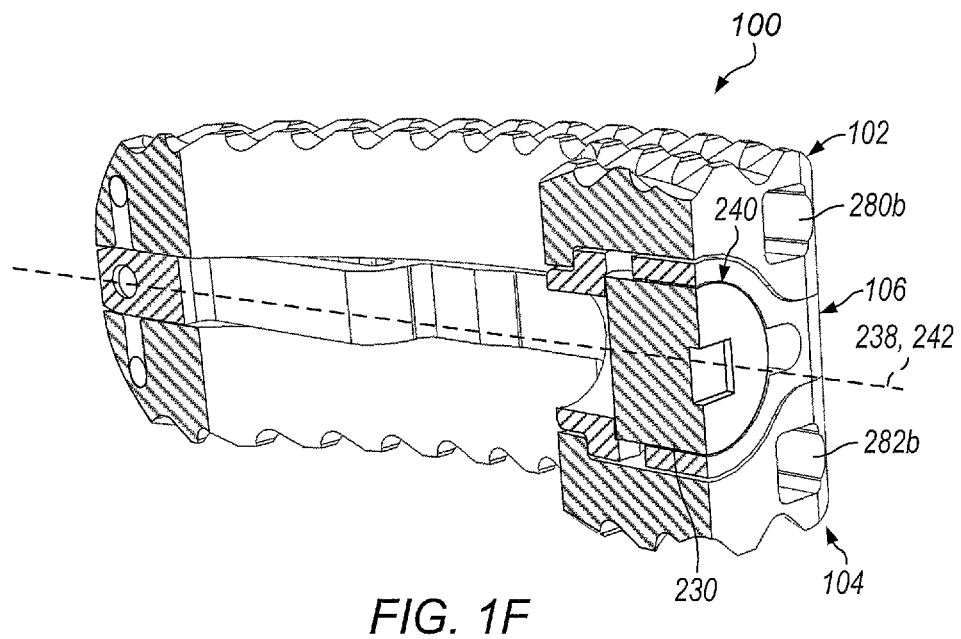
FIG. 1F illustrates a cross-sectioned perspective view of implant taken across line 1F-1F of FIG. 1E in accordance with one or more embodiments of the present technique.
Figure 1H:
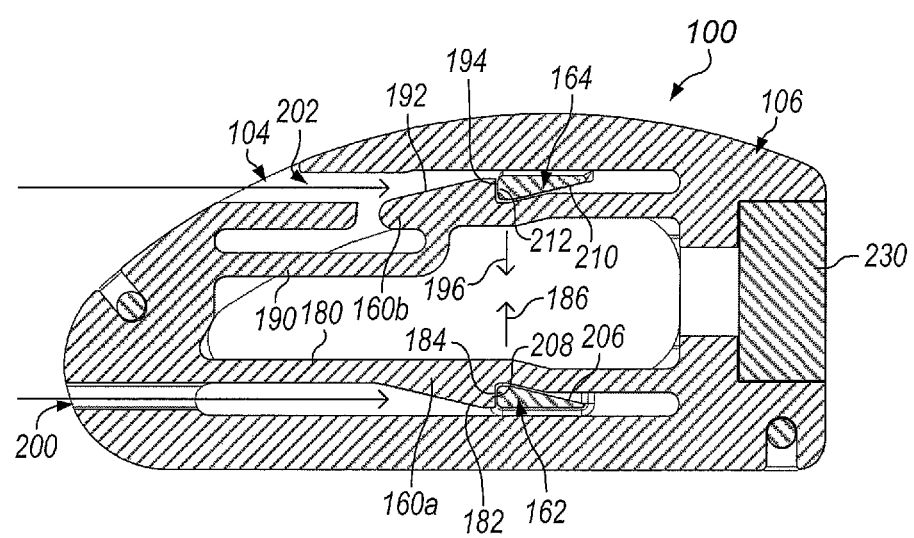
FIG. 1H illustrates a cross-sectioned perspective view of implant taken across line 1H-1H of FIG. 1B in accordance with one or more embodiments of the present technique.
Figure 3D:
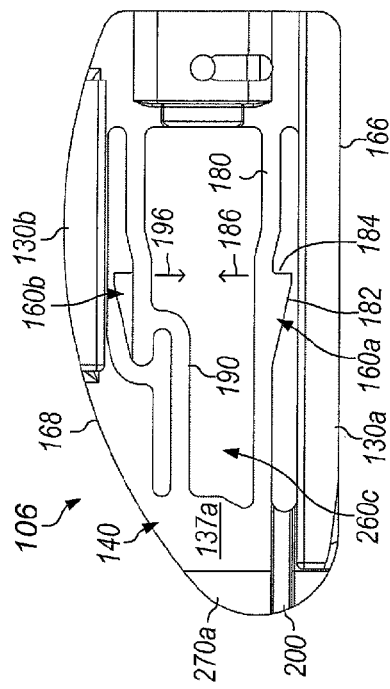
FIGS. 3A, 3B, 3C, 3D, 3E, 3F and 3G depict a perspective view, a side view, a bottom view, a top view, a rear/trailing-end view, a nose/leading-end view, and a side view, respectively of an insert in accordance with one or more embodiments of the present technique.
Figure 3B:
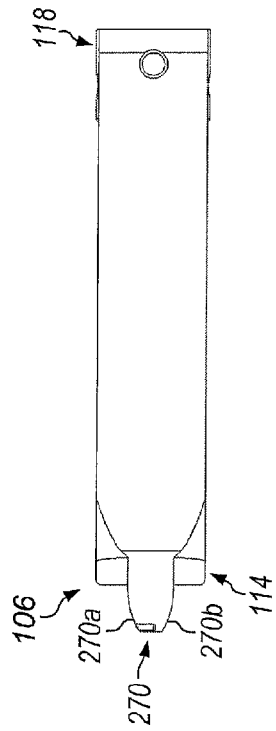
Figure 3A:
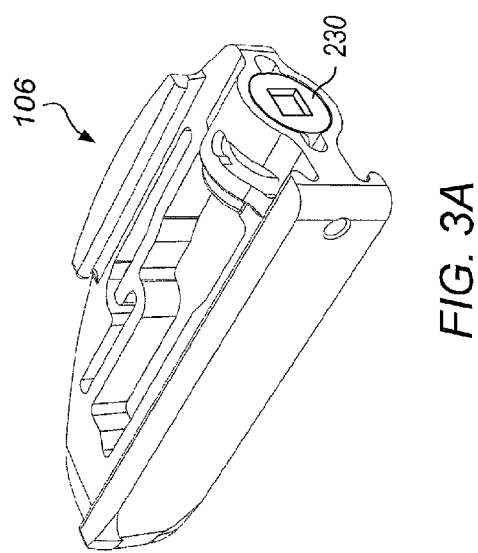
Figure 3E:
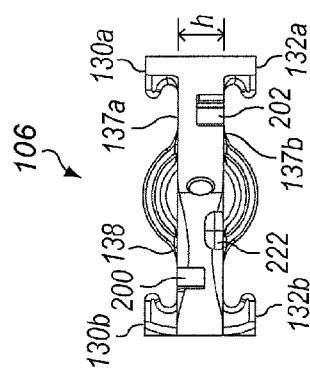
Figure 3F:
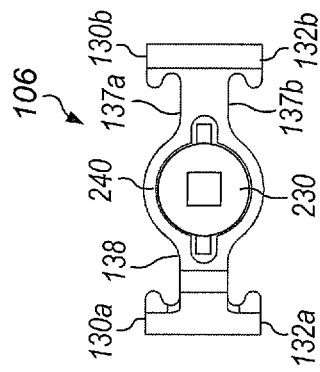
Figure 3G:
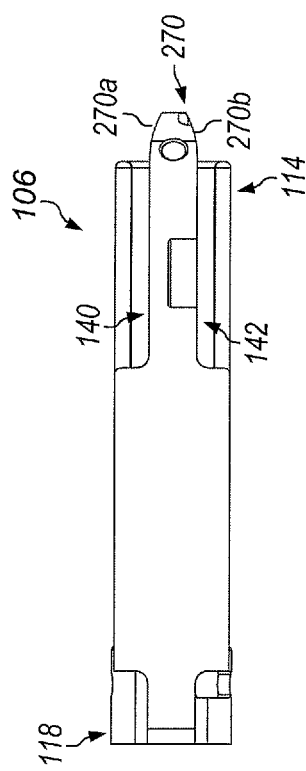
Figure 3C:
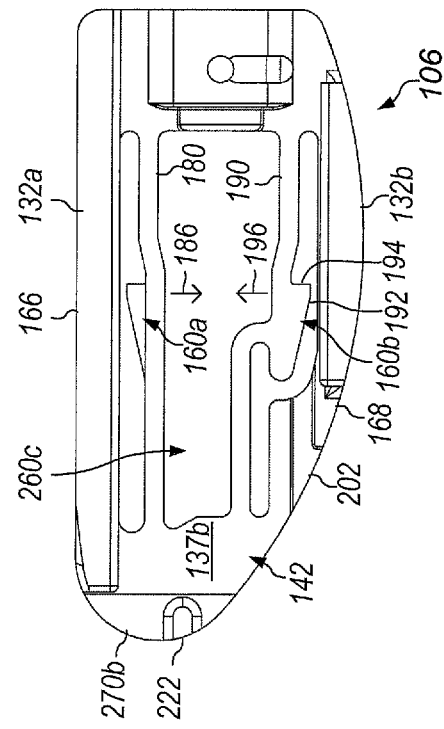

Turning now to the figures, FIG. 1A illustrates a perspective view of an expandable implant system 100 in accordance with one or more embodiments of the present technique. FIGS. 1B, 1C, 1D and 1EF illustrate a left-side view, a back/trailing-end view, a front/leading-end view, and a top view, respectively, of implant 100 in accordance with one or more embodiments of the present technique. FIG. 1F illustrates a cross-sectioned perspective view of implant 100 taken across line 1F-1F of FIG. 1E in accordance with one or more embodiments of the present technique. FIG. 1H illustrates a cross-sectioned perspective view of implant 100 taken across line 1H-1H of FIG. 1B in accordance with one or more embodiments of the present technique.

Implant 100 may include a spinal fusion implant that is disposed between adjacent vertebrae of a human spine. Implant 100 may be expandable such that it is inserted into an intervertebral space in a generally unexpanded configuration, and is subsequently expanded to distract or otherwise maintain the adjacent vertebra at a suitable separation distance. As described in more detail below, expansion of implant 100 and/or maintenance of an expanded height of implant 100 may be provided via insertion of an insert between upper and lower members that engage endplates (or similar bony structures) of the adjacent vertebra. Such an insert may act as a wedge that facilitates distraction and/or a spacer that inhibits contraction of the implant, thereby generating and/or maintaining an expanded height of implant 100 and suitable separation/distraction of the adjacent vertebrae.

In the illustrated embodiment, implant 100 includes an upper member 102, a lower member 104 and an insert 106. FIG. 1A depicts implant 100 in an assembled/expanded configuration wherein insert 106 is disposed between upper and lower members 102 and 104. Implant 100 includes a nose/leading-end 108 and a tail/trailing-end 110. Implant 100 may be inserted into an intervertebral space "nose first". It will be appreciated that relative terms, such as "lower" and "upper" are provided for clarity of description to differentiate between various portions of implant 100. Although certain embodiments of implant 100 and/or insertion/implantation of implant 100 may include components arranged in the described orientations (e.g., upper member 102 is located above lower member 104), other embodiments may include variations in their arrangement. For example, implant 100 may be inverted during insertion such that lower member 104 is located above upper member 102 during insertion/implantation of implant 100.

During use, insert 106 may be advanced linearly between upper and lower members 102 and 104. For example, during implantation of implant 100, upper and lower members 102 and 104 may be disposed within an intervertebral space located between adjacent vertebrae, and insert 106 may be subsequently slid into position between the upper and lower members 102 and 104 to expand or otherwise maintain upper or lower members 102 and 104 in an expanded position to provide for distraction/separation of the adjacent vertebrae. As described in more detail below, advancement of insert 106 may be provided by one or more instruments used to push insert 106 into a gap between upper and lower members 102 and 104. The gap may already exist or may be created by insertion of insert 106.

Figure 2A:
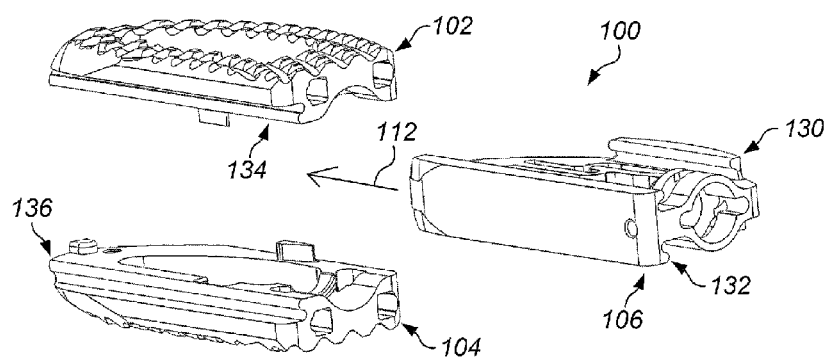
FIGS. 2A and 2B depict perspective and side views, respectively, illustrating insertion of insert between upper and lower members in accordance with one or more embodiments of the present technique.
Figure 2B:
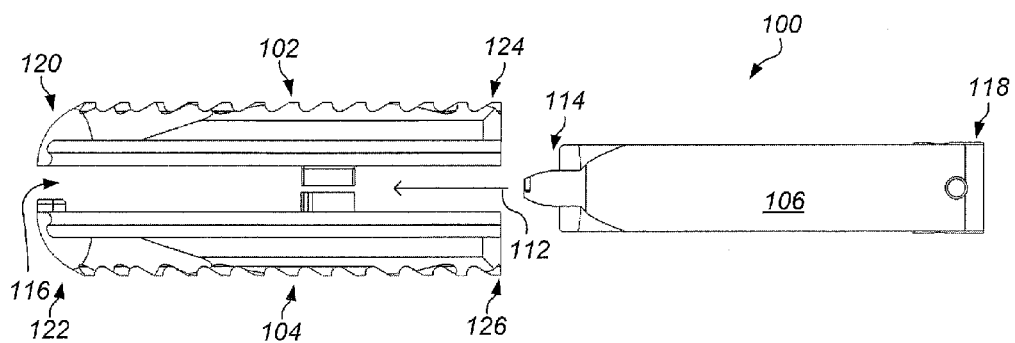

FIGS. 2A and 2B depict perspective and side views, respectively, illustrating insertion of insert 106 between upper and lower members 104 and 106 in accordance with one or more embodiments of the present technique. It will be appreciated that, in FIG. 2A, the spacing between upper and lower members 102 and 104 has been increased to provide a clear view of upper and lower members 102 and 104.

FIGS. 3A, 3B, 3C, 3D, 3E, 3F and 3G depict a perspective view, a side view, a bottom view, a top view, a rear/trailing-end view, and a nose/leading-end view, and a side view, respectively of insert 106 in accordance with one or more embodiments of the present technique. FIGS. 4A, 4B, 4C, 4D, 4E and 4F depict a perspective view, a side view, a bottom view, a top view, a nose/leading-end view and a rear/trailing-end view, respectively of upper member 102 in accordance with one or more embodiments of the present technique. FIGS. 5A, 5B, 5C, 5D, 5E and 5F depict a lower-perspective view, a side view, a bottom view, a top view, a nose/leading-end view, and a rear/trailing-end view, respectively of lower member 104 in accordance with one or more embodiments of the present technique.

During use, upper and lower members 102 and 104 may be separated by a lesser distance (see FIG. 2B) such that portions of inset 106 (e.g., guides) may engage complementary portions (e.g., complementary guides) of upper and lower members 102 and 104, as discussed in more detail below. As depicted, insert 106 may be advanced longitudinally, in a linear direction, as indicated by arrow 112, such that a nose/leading end 114 of insert 106 is advanced into a gap 116 between upper and lower members 102 and 104. Insert 106 may be advanced until nose/leading end 114 and/or a rear/trailing-end 118 of insert 106 is about flush with nose/leading-ends 120 and 122 and/or tail/trailing ends 124 and 126 of upper and lower members 102 and 104, respectively (see FIGS. 1A and 1B).

In some embodiments, advancement of insert 106 between upper and lower members 102 and 104 is guided via one or more guides located on one, or both of insert 106 and/or adjacent portions of upper and lower members 102 and 104. For example, in the illustrated embodiment, a superior surface of insert 106 includes upper guide rails 130a and 130b (referred to collectively as upper guide rails 130) and an inferior surface of insert 106 includes lower guide rails 132a and 132b (referred to collectively as lower guide rails 132). Guide rails 130 and 132 may engage complementary upper guide tracks 134a and 134b (referred to collectively as upper guide tracks 134) of upper member 102 and lower guide tracks 136a and 136b (referred to collectively as lower guide tracks 136) of lower member 104. Although the terms "rails" and "tracks" are used for clarity in distinguishing one from the other, it will be appreciated that the "rails" and "tracks" may include similar/complementary features (e.g., grooves/recess and/or protrusions/lips) that facilitate guiding relative movement and coupling of members 102 and 104 and insert 106.

In the illustrated embodiment, guide rails 130 and 132 of insert 106 run in a substantially longitudinal direction (e.g., extending substantially between tail 118 and nose 114) along superior and inferior surfaces 140 and 142. Similarly, guide tracks 134 and 136 of respective members 102 and 104 run in a substantially longitudinal direction (e.g., extending between tails 124 and 126 and noses 120 and 122). Guide rails and tracks may run along a portion, substantially all or all of a length of insert 106. In the illustrated embodiment, guides rails 130 and 132 run along a length of insert 106 (e.g., from a leading edge portion to a trailing edge portion). Notably, guide rails 132b and 134b are shorter than guide rails 132a and 132a, as the outward curvature of members 102 and 104 creates a shorter effective length. Guides tracks 134 and 136 of members 102 and 104 may extend at least to tail/trailing-ends 124 and 126, and guide rails 130 and 132 of insert 106 may extend at least to nose/leading-end 114 insert 106 such that guide rails 130 and 132 can engage complementary portions of guide tracks 134 and 136 upon insertion of nose-end 114 of insert 106 into tail-ends 124 and 126 of upper and lower members 102 and 104, as illustrated by arrow 112.

In the illustrated embodiment, the guide rails and tracks include complementary shaped protrusions and recesses that engage one another to guide longitudinal/linear advancement of insert 106. For example, rails 130 and 132 include inward-facing undercut grooves, and tracks 136 and 134 include complementary-outward facing undercut grooves. Each of the undercut grooves may define a longitudinally extending lip or dovetailed groove. In the illustrated embodiments, for example, each of the lips/grooves of rails 130 and 132 of insert 106 include an "S" shaped profile that engages a complementary "S" shaped profile of tracks 136 and 134 of upper and lower members 102 and 104. The respective grooves/lips of the rails and tracks may dovetail with one another to guide longitudinal advancement of insert 106 relative to upper and lower members 102 and 104. In some embodiments, engagement of the guide rails and tracks may inhibit lateral shifting and or vertical separation of insert 106 and upper and lower members 102 and 104. For example, the longitudinal orientation and a substantially low tolerance fit between rails 130 and tracks 134 may inhibit lateral (e.g., side-to-side) movement of insert 106 relative to upper member 102, and a similar fit between rails 132 and tracks 136 may inhibit substantial lateral (e.g., side-to-side) movement and rotation of insert 106 relative to lower member 104. Such retention may help to prevent axial rotation of the adjacent vertebrae during the fusion process, thereby facilitating secure bone growth/fusion between the vertebrae. Engagement of the respective lips of the guide rails and tracks may inhibit vertical separation as the overlap between the lips causes them to catch one another. Such retention may help to prevent vertical separation of the adjacent vertebrae during the fusion process, thereby facilitating secure bone growth/fusion between the vertebrae.

In some embodiments, when insert 106 is assembled to upper and lower members 102 and 104, an upper and lower substantially planar exterior surfaces (e.g., superior surface 137a and inferior surface 137b) of a central body portion 138 of insert 106 may abut complementary interior surfaces (e.g., inferior surface 139a and superior surface 139b) of upper and lower members 102 and 104. Abutment of the respective surfaces may resist vertical compression of implant 100, thereby enabling implant 100 to provide for and maintain an expanded height. In the illustrated embodiment, central body portion 138 includes a height (h) such that, when inserted between upper and lower members 102 and 104, the inferior and superior surfaces 139a and 139b of the upper and lower members are separated by a distance about equal to height (h) (see FIG. 3E) and implant 100 has an overall expanded implant height (H) defined by the distance between superior surface 144 of upper member 102 and an inferior surface 146 of lower member 104. Thus, decreasing the height (h) of spacer 106 may provide for a lower overall expanded implant height (H) and increasing the height (h) of spacer 106 may provide for an increased higher overall expanded implant height (H). Height (h) of spacer 106 may include any height to provide any desired height (H). In some embodiments, height (h) is about 0.1 millimeter (mm), 0.2 mm, 0.3 mm, 0.4 mm, 0.5 mm, 0.75 mm, 1 mm, 2 mm, 3 mm, 4 mm, 5 mm, 6 mm, 7 mm, 8 mm, 9 mm, 10 mm, 11 mm, 12, mm, 13 mm, 14 mm, 15 mm or more. In some embodiments, the overall expanded implant height (H) is about 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16, mm, 17 mm, 18 mm, 19 mm, 20 mm or more. In some embodiments, the overall expanded implant height (H) is about 13-17 mm or about 15 mm. As discussed in more detail below, one or a plurality of inserts of different heights may be selected and inserted to achieve a desired overall expanded implant height and resulting separation distance between adjacent vertebrae. For example, an implant kit may include an upper member, a lower member, and a plurality of inserts of differing heights such that an appropriately sized insert can be selected and inserted during a spinal fusion implant procedure.

In some embodiments, implant 100 includes a retaining mechanism to provide for the retention of insert 106 between upper and lower members 102 and 104. For example, in the illustrated embodiment, insert 106 includes an upper retention feature 160a that engages an upper retention peg 162 of upper member 102 and a lower retention feature 160b that engages a lower retention peg 164 of lower member 104. In the illustrated embodiment, upper retention feature 160a is located proximate an internal lateral side 166 of insert 106, lower retention feature 160b is located proximate an external lateral side 168 of insert 106, upper retention peg 162 is located proximate an internal lateral side 170 of upper member 102, and lower retention peg 164 is located proximate an external lateral side 172 of lower member 102. Retention features 160a and 160b may be located within or otherwise coupled to central portion 138 of insert 106. For example, in the illustrated embodiment, retention feature 160a includes a ramped shaped protrusion formed integrally with a cross member 180 of central portion 138. The ramp shaped protrusion includes a leading ramped surface 182 terminating into a substantially orthogonal trailing edge 184 extending substantially laterally with respect to a longitudinal axis (e.g., substantially parallel to the direction of insertion) of insert 106 (See FIG. 3D). In the illustrated embodiment, retention feature 160b includes a similar ramped shaped protrusion formed integrally with a cross member 190 of central portion 138. The ramp shaped protrusion includes a leading ramped surface 192 terminating into a substantially orthogonal trailing edge 194 (See FIG. 3C). In some embodiments, cross-members 180 and/or 190 may be flexible such that the ramped shaped protrusion may translate inward in the direction of arrows 186 and 196, respectively when ramped surfaces 182 or 192 are engaged by complementary upper and lower retention pegs 162 and 164, respectively. For example, in the illustrated embodiment cross members 180 and 190 include relatively thin-elongated shaped members formed from adjacent cut-outs within central portion 138. The thin elongate cross-section may enable lateral deflection of retention features 160a and 160b.

In the illustrated embodiment, retention features 160a and 160b are recessed within central body portion 138 such that they do not extend beyond superior and inferior surfaces 137a and 137b of central body portion 138 of insert 106. Central body portion 138 includes slots 200 and 202 that provide for longitudinal insertion/sliding of retention pegs 162 and 164 into engagement with the recessed retention features 160a and 160b. For example slot 200 is formed in superior surface 137a and extends from an area proximate retention feature 160a to a leading edge of insert 106 to provide a channel that enables retention peg 162 to slide there through as insert 106 is advanced between upper and lower members 102 and 104. Slot 202 is formed in inferior surface 137b and extends from an area proximate retention feature 160b to a leading edge of insert 106 to provide a channel that enables retention peg 164 to slide there through as insert 106 is advanced between upper and lower members 102 and 104.

Retention peg 162 includes a protrusion extending downward from inferior surface 139a of upper member 102. The protrusion includes a ramped trailing surface 206 terminating into a substantially orthogonal leading edge 208. Similarly, retention peg 164 includes a protrusion extending upward from superior surface 139b of lower member 104. The protrusion includes a ramped trailing surface 210 terminating into a substantially orthogonal leading edge 212.

FIG. 1H depicts a cross-sectioned view of implant 100 having insert 106 installed therein. The figure illustrates retention pegs 162 and 164 in a locked position with respect to retaining features 160a and 160b. For example, trailing edges 194 and 184 of insert 106 abut leading edges 212 and 208 of the pegs 162 and 164 of upper and lower members 102 and 104.

During use, insert 106 may be advanced between upper and lower members 102 and 104 (as described below with respect to FIGS. 9A-9F) such that pegs 162 and 164 are advanced into and through slots 200 and 202, respectively, and leading ramped surfaces 192 and 182 of retaining features 160a and 160b engage the complementary ramped trailing surfaces 206 and 210 of pegs 162 and 164, respectively. Upon further forward advancement of insert 106, leading ramped surfaces 192 and 182 of retaining features 160a and 160b slidingly engage the complementary ramped trailing surfaces 206 and 210 of pegs 162 and 164, thereby creating an inward biasing force that causes cross-members 180 and 190 and retaining features 160a and 160b to deflect inward in the direction of arrows 186 and 196. Upon further forward advancement of insert 106, trailing edges 184 and 194 of retaining features 160a and 160b may be moved into a position at or just past leading edges 208 and 212 of pegs 162 and 164 such that retaining features 160a and 160b snap back into their undeflected/locked position with respect to retaining features 160a and 160b. For example, trailing edges 194 and 184 of insert 106 abut leading edges 212 and 208 of the pegs 162 and 164 of upper and lower members 102 and 104. The snap of retaining features 160a and 160b may provide cound or tactile sensation (e.g., audible and/or physical sensation) that alerts a user (e.g., a surgeon) that insert 106 has been fully engaged and is properly seated between upper and lower members 102 and 104. Thus, reducing the risk of insert 106 not being fully inserted and potentially backing-out post operatively.

In the illustrated embodiment, a forward peg 220 extending from lower member 102 engages a complementary recess/slot 222 of insert 106 to limit additional forward movement of insert 106, thereby inhibiting over insertion of insert 106. A similar recess/slot 222 may be provided on upper member 102. The combination of the forward stopping mechanism along with the retaining mechanism may facilitate proper placement of insert 106 by inhibiting over insertion and back-out of insert 106.

In some embodiments, an actuatable locking mechanism may provide for at least partial retention of insert 106 between upper and lower members 102 and 104. In the illustrated embodiment, insert 106 includes a locking member 230. FIGS. 6A, 6B and 6C illustrate a perspective view, a rear-end view and a side view, respectively, of rotating locking member 230, in accordance with one or more embodiments of the present technique. FIGS. 7A and 7B illustrate actuation of locking member 230 within implant 100, in accordance with one or more embodiments of the present technique.

In the illustrated embodiment, locking member 230 includes a cylindrical body 232, two protruding arms 234a and 234b, and a tool recess 236. During use cylindrical body 232 is inserted into a complementary cylindrical recess 240 within a trailing end of insert 106. Recess 240 may include two lateral recess 240a and 240b extending radially. Insert 106 may be inserted such that its longitudinal axis 238 substantially aligns with a longitudinal axis of recess 240 and or a longitudinal axis 242 of insert 106 and/or implant 100. During insertion, arms 234a and 234b of locking member 230 may be aligned and inserted into lateral recess 240a and 240b, respectively, such that locking member 230 is advanced longitudinal into recess 240. During use, locking member 230 may be rotated such that arms 234a and 234b engage complementary recess of upper and/or lower members 102 and 104. For example, as illustrated in FIGS. 7A and 7B, locking member 230 may be rotated about longitudinal axis 238 from an unlocked position, in which arms 234a and 234b are not engaged with upper and lower members 102 and 104, to a locked position in which arms 234a and 234b are rotated into engagement with recesses 244a and 244b of upper member 102 and lower member 104, respectively, as depicted by arrow 246. Rotation may be provided via a tool engaging tool recess 236 and being rotated. Recesses 244a and 244b may include notches that, when engaged by arms 234a and 234b, block/inhibit forward and/or backward movement of locking member 230 relative to upper and lower member 102 and 104. Arms 234a and 234b may be rotated into and extend through slots within insert 106 such that insert is blocked/inhibited forward and/or backward movement relative to locking member 230. Thus, upon actuation/rotation of locking member 230, insert 106 may be locked to upper and lower members 102 and 104, thereby further inhibiting back-out of insert 106.

In the illustrated embodiments, locking member 230 is rotated about forty-five degrees about axis 238 between the locked and unlocked positions. Other embodiments may include varying amounts of rotations. For example, locking member 230 may be rotated about five, ten, fifteen, twenty, twenty-five, thirty, thirty-five, forty, fifty, fifty-five, sixty, seventy, seventy-five, eighty, eighty-five, ninety degrees or more between the locked and unlocked positions.

Outer surfaces of upper and/or lower members 102 and 104 may include various features to facilitate engagement of their exterior surfaces with endplates of adjacent vertebrae. For example, as illustrated in FIGS. 4D and 5C, superior surface 144 of upper member 102 and inferior surface 146 of lower member 104 may include protrusions (e.g., teeth) 250 extending there from. During use, teeth 250 may extend/penetrate into adjacent boney structure of the upper and lower adjacent vertebrae. Such penetration may help to fix a position of upper and lower members 102 and 104, and, thus assembled implant 100, relative to the vertebrae. Fixing or otherwise stabilizing the implant may reduce the likelihood of implant 100 being expelled from within the intervertebral space, and may promote bone attachment to and through implant 100.

In some embodiments, protrusions 250 may include unidirectional teeth that facilitate forward insertion of the members, but inhibit back-out of the members. For example, in the illustrated embodiment, teeth 250 include a ramped leading surface 250a and a substantially vertical trailing edge 250b (see FIGS. 4B and 5B). Thus, forward advancement of the members may be facilitated as boney structure of the vertebrae slides over ramped leading surface 250a of teeth 250 and backward advancement may be inhibited by substantially vertical trailing edge 250b hooking into or otherwise engaging the boney structure of the vertebrae.

Protrusions 250 may be provided in a variety of shapes and patterns. In the illustrated embodiment, protrusions 250 include six arched shaped rows of teeth arranged in a generally concentric pattern. The arched rows have a profile that is substantially similar to the curvature of lateral external edges 172 and 173 of upper and lower members 102 and 104.

In some embodiments, implant 100 includes one or more openings extending vertically between upper and lower surfaces of implant 100. For example, in the illustrated embodiment, implant 100 includes a vertical opening 260 defined openings 260a, 260b and 260c extending vertically through upper member 102, lower member 104 and insert 106, respectively. Vertical opening 260 may be provided when implant 100 is assembled to include insert 106 fully inserted/seated between upper and lower members 102 and 104 such that opening 260a, 260b and 260c substantially aligned with one another. Vertical opening may extend completely through implant 100, from superior surface 144 of upper member 102 to inferior surface 146 of lower member 104. In some embodiments, vertical opening 260 may be filled with a substance/material to facilitate bone growth/fusion. Once implant 100 is implanted, vertical opening may facilitate a column of bone growth between the adjacent vertebrae through vertical opening 260. In some embodiments, an opening (e.g., opening 260) may function as a graft window containing bone chips and/or materials which facilitate tissue (e.g., bone) growth.

In some embodiments, insert 106 may act as a wedge that provides for increasing a separation distance between upper and lower members 102 and 104 (e.g., such that the adjacent vertebra are distracted as insert 106 is installed) and/or a spacer that is advanced between upper and lower members 102 and 104 to maintain a separation distance there between (e.g., where upper an lower members 102 and 104 have already been separated/distracted an adequate amount prior to insertion of insert 106). In some embodiments, insert 106 includes a tapered/wedged shaped nose/leading-end that facilitates insertion of insert 106. For example, in the illustrated embodiment, insert 106 includes a tapered/ramped/wedge shaped nose portion 270 (see FIG. 3B). Nose portion 270 includes upper and lower ramped surfaces 270a and 270b that terminate into a substantially flat/planar portion of superior and inferior surfaces 137a and 137b of central body portion 138. Thus, when interior surfaces of upper and lower members 102 and 104 (e.g., inferior surface 139a and superior surface 139b) are separated by less than height (h) of central body portion 140, ramped surfaces 270a and 270b may engage trailing end portions of inferior surface 139a and superior surface 139b. As insert 106 is advanced, nose portion 270 may facilitate spreading of the upper and lower members 102 and 104 to enable further distraction of members 102 and 104 and advancement of insert 106.

In some embodiments, one or more tool/instruments may be used to facilitate expansion of implant 100. For example, expansion instruments coupled to upper member and lower member 102 and 104 may generate a distraction force that separates the members, thereby increasing a size of gap 116 to enable insert 106 to be provided therein. In some embodiments, the distraction force may be sufficient to expand gap 116 to accept insert 106 without much or any additional distraction. For example, the gap 116 may have a height approximately equal to height (h) of insert 106. In some embodiments, the distraction force may help to expand gap 116, however, advancement of insert 106 between upper and lower members 102 and 104 may provide for additional distraction to fully expand implant 100. For example, the distraction forces may partially distract upper and lower members 102 and 104, and advancement of insert 106 may act as a wedge, providing additional distraction forces that, alone or combined with the distraction forces of the instruments, provides additional distraction to fully expand implant 100.

In the depicted embodiments, implant 100 includes tool engagement features that enable coupling of one or more instruments to upper and lower members 102 and 104. For example, upper member 102 includes recess 280a and 280b, and lower member 104 includes tool recesses 282a and 282b (see FIGS. 4F, 5F and 1F). Each of recesses 280a, 280b, 282a and 282b extend into rear/trailing ends of the respective upper and lower members 102 and 104. During use, a protrusion of a complementary instrument may be engaged into one or more of the recess. For example, two protrusions of an upper instrument portion may be inserted into recesses 280a and 280b and two protrusions of a lower instrument portion may be inserted into recesses 282a and 282b. Applying a spreading force to the upper and lower instrument portions may generate a corresponding distraction force that is transferred to the upper and lower members 102 and 104, thereby aiding in generating and/or widening of gap 116. The spreading force may be maintained as insert 106 is advanced between upper and lower members 102 and 104.

As discussed in more detail below, the upper and lower instrument portions may include or may be attached to elongate instrument extensions that can be used to guide insertion of upper and lower members 102 and 104 into the intervertebral space. Insertion, placement and/or aligning of implant 100 within the intervertebral space may be accomplished using the instruments. Some or all of recesses 280a, 280b, 282a and 282b may include a retention feature that at least partially couples the instrument portions to the respective upper and lower member 102 and 104. For example, an interior of some or all of recesses 280a, 280b, 282a and 282b may include a detent feature (e.g., recess) that engages a complementary detent feature (e.g., protrusion) of the instrument portions such that the protrusion and, thus, the instrument portion can be clipped to the recess. Once upper and lower members 102 and 104 are positioned appropriately within the intervertebral space, pulling on the instrument portions may overcome the coupling of the detent features, thereby enabling release of the instrumentation from implant 100.

The upper and lower instrument portions may include guide tracks that couple to guide rails of insert 106 to facilitate guiding of insert 106 into gap 116. For example, an inferior surface of on upper instrument portion and a superior surfaced of a lower instrument portion may include guide track similar to guide tracks 134 and 136 of upper and lower members 102 and 104. When the instrument portions are coupled to upper and lower members 102 and 104, the guide tracks of the instruments may align with guide tracks 134 and 136 of members 102 and 104 to provide an elongated track to guide insertion of insert 106. For example, insert 106 may be advanced along a longitudinal path that extends across the guide tracks of the instruments and guide tracks 134 and 136.

FIGS. 8A, 8B, 8C and 8D illustrate a perspective view, a side view, an end view, and a top view of a guide instrument 290, in accordance with one or more embodiments of the present technique. Guide instrument 290 includes an elongate body 292 having a guide surface 294. Depending on the orientation of guide instrument, guide surface 294 may be located on an inferior surface or inferior surface of guide instrument 290. In the illustrated embodiment, guide surface is located on a superior/top/upper surface of guide instrument 290. Guide surface 294 includes guide tracks 296a and 296b (referred to collectively as guide tracks 296). Guide tracks 296 may have a profile that is the same or similar to guide tracks 134 and 136 of upper and lower members 102 and 104. For example, guide tracks 296 include outward facing undercut grooves that are shaped complementary to guide rails 130 and/or 132 of insert 106. Each of the undercut grooves may define a longitudinally extending lip or dovetail. In the illustrated embodiments, for example, the lips/grooves include an "S" shaped profile that engages a complementary "S" shaped profile of insert 106. The respective grooves/lips of guide rails 130 and/or 132 and guide tracks 294 may dovetail with one another to guide longitudinal advancement of insert 106 relative to the guide instrument 290 and/or upper and lower members 102 and 104.

A front/leading end of guide instrument 290 includes protrusions 298a and 298b (collectively referred to as guide protrusions 298). In the illustrated embodiments, protrusions 298a and 298b include elongate cylindrical shaped protrusions that, during use, engage recesses 280a and 280b of upper member 102 or 282a and 282b of lower member 104. Protrusions 298 may provide for aligning of guide tracks 294 with guide tracks 134 and 136 of upper and lower members 102 and 104 when instrument 290 is coupled to upper or lower member 102 or 104. Protrusions 298 may include detent features that engage complementary detent features of upper or lower members 102 or 104 to facilitate coupling of instrument 290 to upper or lower members 102 or 104. In the illustrated embodiment, protrusions 298a and 298b include respective detent catches 300a and 300b. Detent catches 300a and 300b may couple to complementary detent pockets 302 within recess 280a, 280b, 282a, or 282b. Coupling of detent may facilitate retention of instrument 290 to upper or lower members 102 or 104 during insertion. Detent features may facilitate removal of instrument 290 from upper or lower members 102 or 104 via application of a longitudinal separation force pulling instrument 290 away from upper or lower members 102 or 104. Detent features may enable instrument 290 to be snapped into and out of upper or lower members 102 or 104.

Figure 9A:
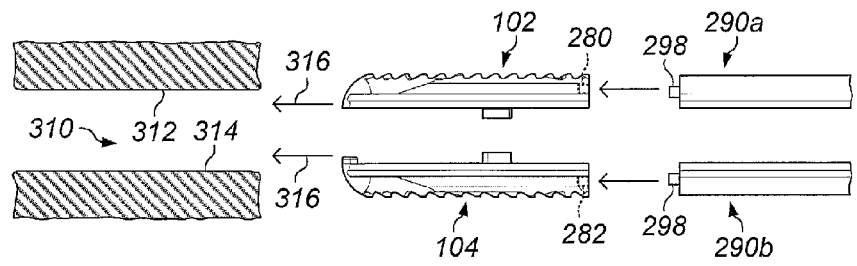
FIGS. 9A-9F illustrate a sequence of implanting implant in accordance with one or more embodiments of the present technique.
Figure 9B:
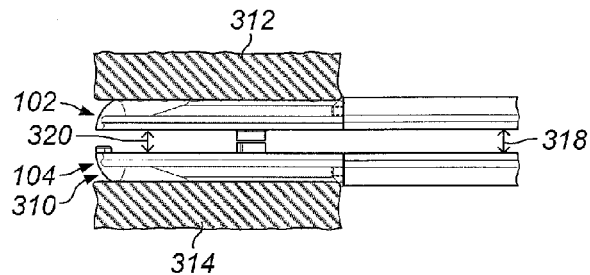
Figure 9C:
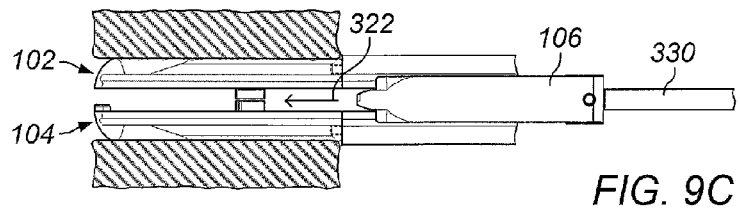
Figure 9D:
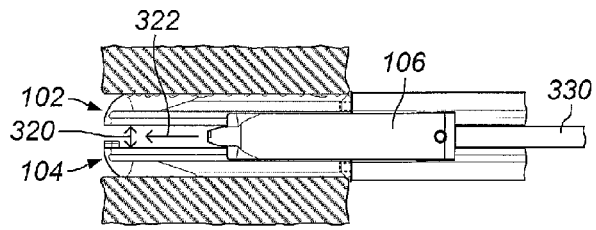
Figure 9E:
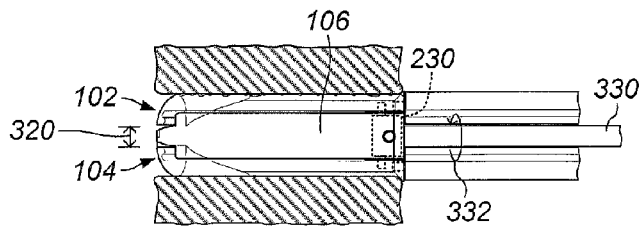
Figure 9F:
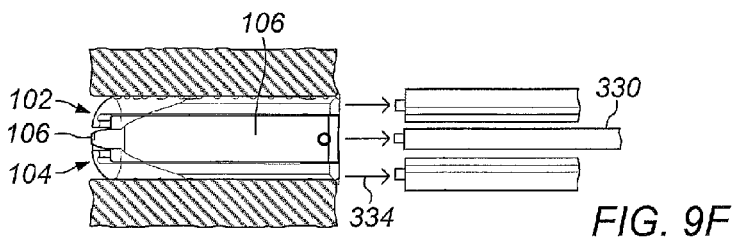
Figure 10:
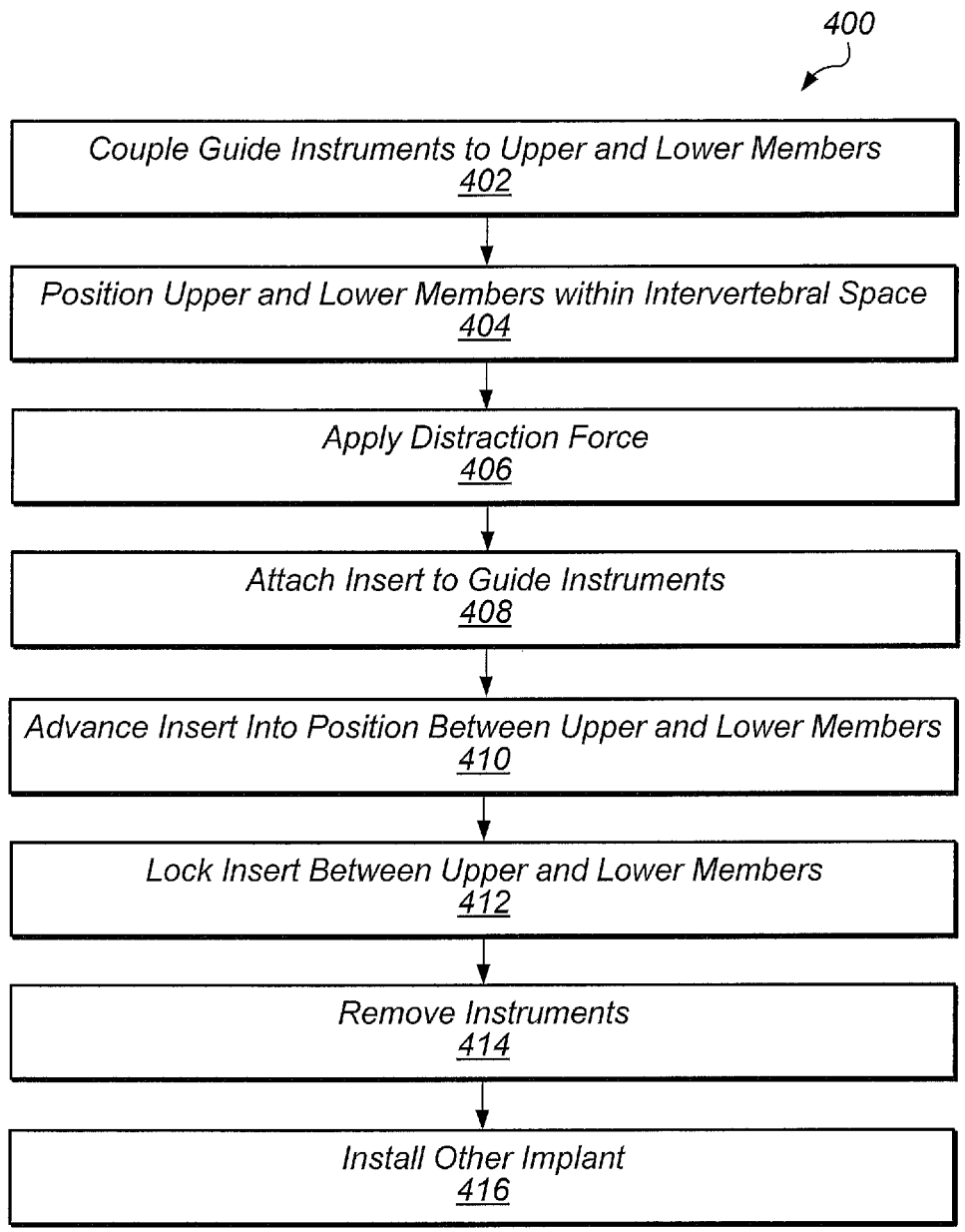
FIG. 10 is a flowchart that illustrated a method for implanting implant in accordance with one or more embodiments of the present technique.

FIGS. 9A-9F illustrate a sequence of implanting implant 100 in accordance with one or more embodiments of the present technique. As depicted, implant 100 is disposed within an intervertebral space 310 between adjacent vertebrae 312 and 314. FIG. 10 is a flowchart that illustrated a method 400 for implanting implant 100 in accordance with one or more embodiments of the present technique. Method 400 generally includes coupling guide instruments to upper and lower members of an implant, positing the upper and lower members within an intervertebral space, applying a distraction force, attaching an insert to the guide instruments, advancing the insert into position between the upper and lower members, locking the insert between the upper and lower members, and removing the guide instruments. In some embodiments, method 400 includes installing another implant.

Method 400 may include coupling guide instruments to upper and lower members, as depicted at block 402. In some embodiments, coupling guide instruments to upper and lower members includes coupling an upper guide 290a instrument to upper member 102 and a lower guide instrument 290b to lower member 104, as depicted in FIG. 9a. For example, instrument protrusions 298 of upper guide instrument 290a may be inserted into recesses 280 of upper member 102 such that detents 300 engage pockets 302 of the recesses. Instrument protrusions 298 of lower guide instrument 290b may be inserted into recess 280 of lower member 104 such that detents 300 engage pockets 302 of the recesses.

Method 400 may include positioning the upper and lower members within an intervertebral space, as depicted at block 404. In some embodiments, positioning the upper and lower members within an intervertebral space may include disposing upper member 102 and/or lower member 104 within intervertebral space 310 between upper vertebra 312 and lower vertebra 314, as depicted in FIG. 9B. When positioned, superior surface 144 of upper member 102 may abut an endplate, or other boney structure of, upper vertebra 312 and inferior surface 146 of lower member 104 may abut an endplate, or other boney structure, of lower vertebra 314. For example, teeth 250 may engage the boney structure of vertebrae 312 and 314. Insertion of upper and lower members 102 and 104 may be accomplished by a practitioner handling trailing end portions of guide instruments 290a and 290b to move upper and lower members 102 and 104 into intervertebral space 310 as represented by arrows 316. In some embodiments, each of upper and lower members 102 and 104 may be positioned individually. For example, lower member 104 may be positioned in intervertebral space 310, followed by positioning of upper member 102 within intervertebral space 310. In some embodiments, upper and lower members 102 and 104 may be positioned substantially simultaneously. For example, upper and lower members 102 and 104 may be coupled to one another and/or upper and lower guide instruments 290a and 290b may be rigidly coupled such that both of upper and lower members 102 and 104 are moved in unison into intervertebral space 310.

Method 400 may include applying a distraction force, as depicted at block 406. In some embodiments, applying a distraction force includes applying a force to urge lower body and upper body away from one another. For example, a spreading force may be applied to upper and lower guide instruments 290a and 290b, as depicted by arrow 318. In some embodiments, the spreading force is generated by a practitioner simply spreading/pushing/pulling the upper and lower guide instruments 290a and 290b away from one another. In some embodiments, the spreading force is generated mechanically. For example, lower guide instruments 290a and 290b may be coupled to one another via spreading pliers, such that squeezing the pliers generates a spreading force that urges the lower guide instruments 290a and 290b away from one another. In some embodiments, the pliers may include a ratcheting mechanism such that incremental increases in separation distances can be achieved between guide instruments 290a and 290b. The spreading force may be transferred to upper and lower members 102 and 104 (e.g., via engagement of protrusions 298 with recesses 280 and 282) to generate a corresponding spreading force to upper and lower members 102 and 104, as depicted by arrows 320. The spreading force may cause actual separation/distraction of lower guide instruments 290a and 290b, upper and lower members 102 and 104, and/or upper and lower vertebrae 312 and 314. In some embodiments, the spreading force may simply counteract some of the compressive forces between vertebrae 312 and 314, however, the spreading force may not cause any substantial separation/distraction of lower guide instruments 290a and 290b, upper and lower members 102 and 104, and/or upper and lower vertebrae 312 and 314

Method 400 may include attaching an insert to the guide instruments, as depicted at block 408. In some embodiments, attaching an insert to the guide instruments includes attaching insert 106 to one or both of guide instruments 290a and 290b. For example, in the illustrated embodiment, guide rails 130 and 132 are coupled to guide tracks 296 of the respective upper and lower guide instruments 290a and 290b. In some embodiments, guide tracks 296 may guide longitudinal sliding of insert 106 between guide instruments 290a and 290b such that insert 106 can be slid from at or near a trailing end of guide instruments 290a and 290b, past the leading end of guide instruments 290a and 290b and onto guide tracks 134 and 136 of upper and lower members 102 and 104.

In some embodiments, an insert instrument 330 engages insert 106. Insert instrument 330 may be used to push/pull insert along the guide tracks. In some embodiments, insert instrument 330 includes a keyed leading end that engages tool recess 236 of locking member 230. Insert instrument 330 may be used to advance insert 106 and/or actuate locking member 230 to lock insert 106 between upper and lower members 102 and 104.

Method 400 may include advancing the insert into position between the upper and lower members, as depicted at block 410. In some embodiments, advancing the insert into position between the upper and lower members may include pushing insert 106 forward in the direction of arrow 322, as depicted in FIGS. 9C and 9D. With guide tracks 296 of upper and lower guide instruments 290a and 290b longitudinally aligned with respective guide tracks 134 and 136 of upper and lowers bodies 102 and 104, effective upper and lower unitary guide tracks may be formed to enable sliding of insert 106 forward from a location between guide instruments 290a and 290b (see FIG. 9C), into a location at least partially between upper and lower members 102 and 104 (see FIG. 9D). Spacer 106 may be advanced until completely inserted between upper and lower members 102 and 104. For example, spacer 106 may be advanced until nose/leading end 114 and/or a rear/trailing-end 118 of insert 106 is about flush with nose/leading-ends 120 and 122 and/or tail/trailing ends 124 and 126 of upper and lower members 102 and 104, respectively (see FIG. 9E). In some embodiments, advancement maybe limited by forward peg 220 of lower member 102 engaging complementary recess/slot 222 of insert 106, thereby inhibiting over insertion of insert 106. Once installed, back-out of insert 106 may be inhibited by retention features 160 engaging complementary pegs 162 and 164 of upper and lower members 102 and 104. In some embodiments, complete insertion is signaled by engagement of peg 220 into slot/recess 222 and/or engagement of retention features 160. For example, an audible click may be heard and/or a tactile sensation may be felt as the retention features and/or the peg are engaged.

Advancement of insert 106 may provide additional distraction forces that combine with the distraction forces provided at block 406 to effectively distract vertebrae 312 and 314. For example, nose of 114 of insert 106 may act as a wedge to distract upper and lower members 102 and 104. Where the distraction force at block 406 is sufficient to distract upper and lower members 102 and 104, insert 106 may simply inserted to act as a spacer to maintain the distraction. Once inserted, insert 106 may be left in place to act as a spacer that maintains implant 100 at the distracted/expanded height.

Method 400 may include locking the insert between upper and lower members, as depicted at block 412. In some embodiments, locking the insert between upper and lower members includes actuating/rotating locking member 230 such that arms 234a and/or 234b engage recesses 244a and 244b of upper member 102 and lower member 104, respectively. For example, insert instrument 330 may be rotated about longitudinal axis 238, as indicated by arrow 332, such that the keyed leading end engages tool recess 236 of locking member 230, thereby transmitting a torque to rotate locking member into a locked position (see FIGS. 7A, 7B and 9E).

Method 400 may include removing the instruments, as depicted at block 414. In some embodiments, removing the instruments includes removing some or all of upper guide instrument 290a, lower guide instrument 290b and insert instrument 330. For example, a practitioner may simply pull each of the instruments backwards to de-couple them from the respective portions of implant 100, as depicted by arrows 334 of FIG. 9F.

Figure 11:
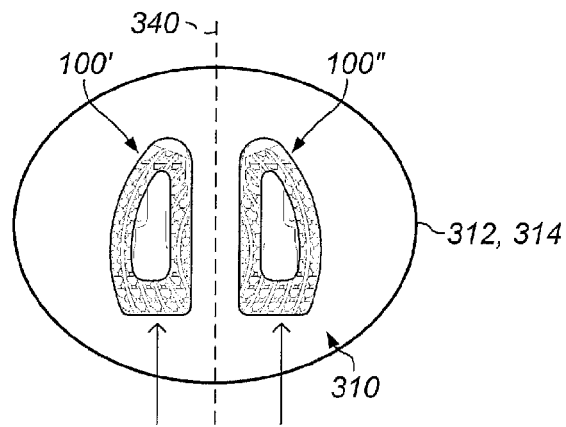
FIG. 11 illustrates installation of multiple implants in accordance with one or more embodiments of the present technique.

Method 400 may include installing other implants, as depicted at block 416. In some embodiments, installing other implants may include installing another implant with intervertebral space 310 and/or another intervertebral space between other adjacent vertebrae. For example, as depicted in FIG. 11, a first implant 100' may be implanted on a first side of a saggital plane 340 of vertebrae 312 and 314, and a second implant 100" may be implanted on a second/opposite side of saggital plane 340, such that a pair of intervertebral implants are implanted within intervertebral space 310. Each of implants 100' and 100" may be similar to implant 100, and may be implanted a method that is the same or similar to method 400. In some embodiments, an implant may be inserted at an oblique angle to saggital plane 340. For example, a single implant (e.g., implant 100) or multiple implants (e.g., implants 100' and 100") may be disposed in the intervertebral space at angle of about forty-five degrees relative to saggital plane 340.

It will be appreciated that method 400 is an exemplary embodiment of a method employed in accordance with techniques described herein. Method 400 may be may be modified to facilitate variations of its implementations and uses. The order of method 400 may be changed, and various elements may be added, reordered, combined, omitted, modified, etc.

Figure 12A:
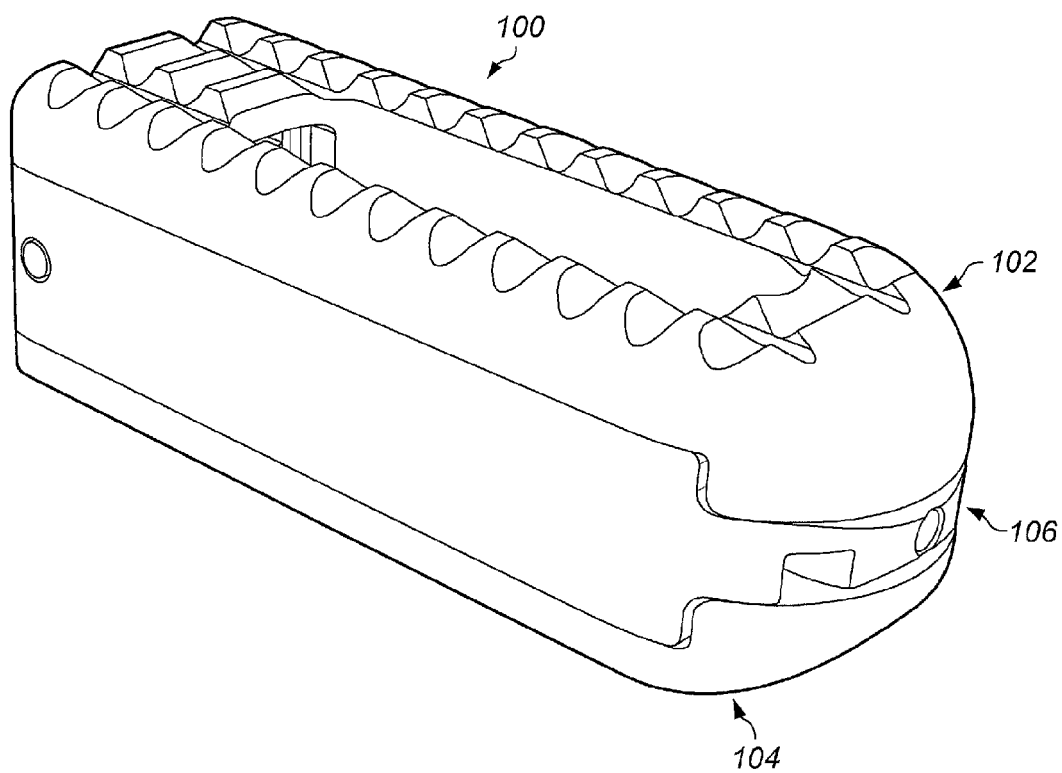
FIGS. 12A-12B illustrates a perspective view of an expandable implant system in accordance with one or more embodiments of the present technique.
Figure 12B:
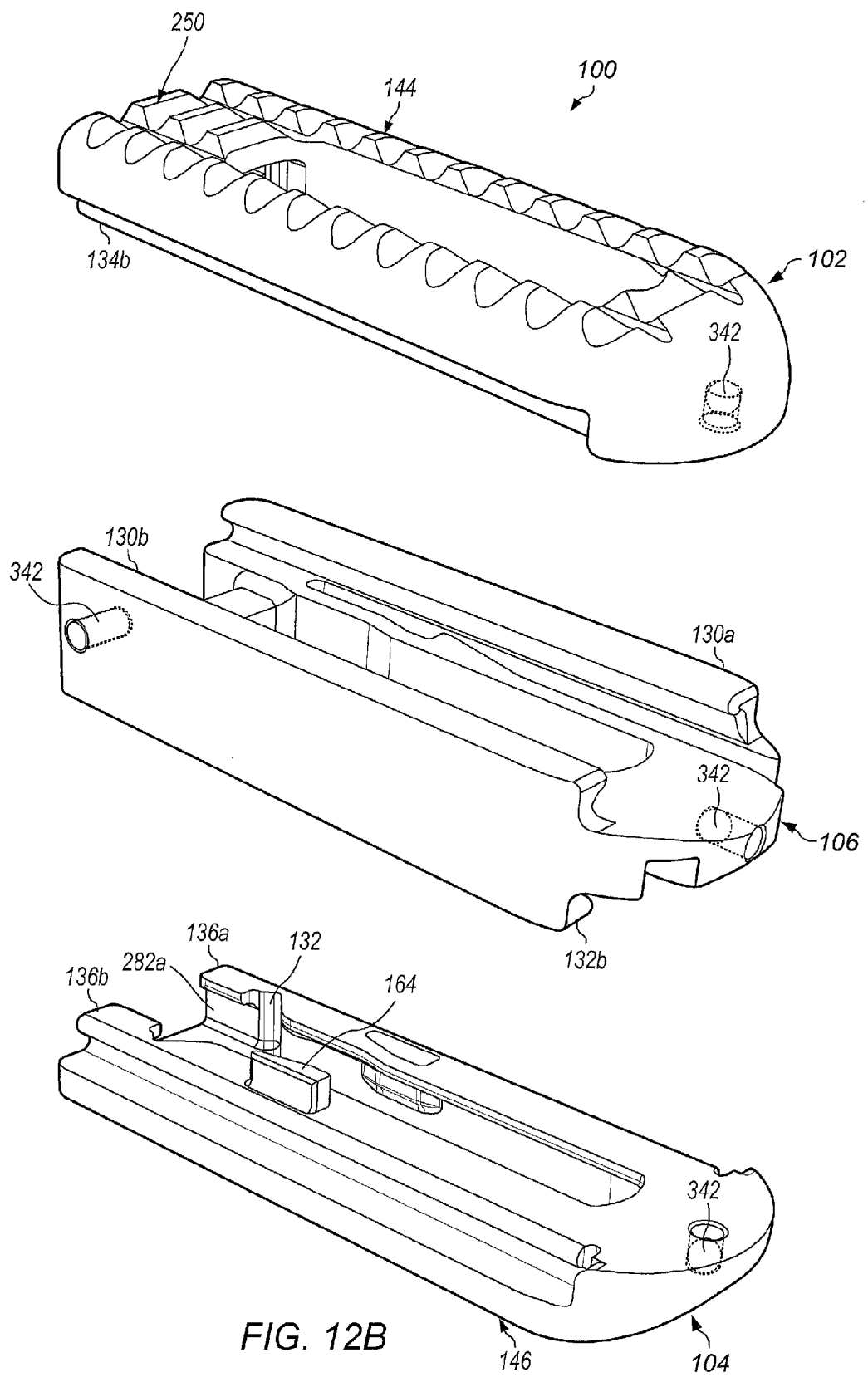

FIGS. 12A-12B illustrates a perspective view of expandable implant system 100 in accordance with one or more embodiments of the present technique. In some embodiments, one or more portions of expandable implant system 100 may include markers 342. Markers may be used to assess a position of one or more portions of the expandable implant system during implantation in a subject. A portion of the expandable implant system may include none, one or multiple markers. Markers may provide radiographic opacity. Markers may be biocompatible. Markers may be of any size or shape. In some embodiments, a system may have multiple markers with different shapes in order to more easily identify different portions of the system and/or an orientation of one or more portions of the system. In FIG. 12B, markers 342 include spherical and rod shapes. In some embodiments, one or more markers may be formed from gold or tantalum.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Furthermore, note that the word "may" is used throughout this application in a permissive sense (i.e., having the potential to, being able to), not a mandatory sense (i.e., must). The term "include", and derivations thereof, mean "including, but not limited to". As used throughout this application, the singular forms "a", "an" and "the" include plural referents unless the content clearly indicates otherwise. Thus, for example, reference to "a member" includes a combination of two or more members. The term "coupled" means "directly or indirectly connected".

What is claimed is:

1. An intervertebral implant configured to be implanted within an intervertebral space between endplates of adjacent vertebra during use, the implant comprising:
   a first member comprising:
      an interior surface comprising a first guide track; and
      an exterior surface configured to contact an endplate of a first of the adjacent vertebra during use;
   a second member comprising:
      an interior surface comprising a second guide track; and
      an exterior surface configured to contact an endplate of a second of the adjacent vertebra during use; and
   an insert comprising:
      a first exterior surface comprising a first guide rail configured to engage the first guide track during use; and
      a second exterior surface comprising a second guide rail configured to engage the second guide track during use, wherein engagement of the first and second guide rails with the first and second guide tracks, respectively, guides insertion of the insert between the first and second members during use, and wherein insertion of a tapered insertion end of the insert between the first and the second members expands the intervertebral implant such that a separation distance between the first and the second members is increased;

an actuatable locking mechanism coupling the insert to the first and second members of the implant during use to inhibit back-out of the insert from between the first and second members, wherein the locking mechanism is rotatably actuatable between a locked position and an unlocked position, and wherein the locking member comprises one or more members that substantially simultaneously engage at least a first locking recess of the first member and at least a second locking recess of the second member during use.

2. The implant of claim 1, wherein the insert comprises a retaining feature, wherein at least one of the first and second members comprises a complementary retaining feature configured to engage the retaining feature of the insert to inhibit back-out of the insert from between the first and second members during use.

3. The implant of claim 2, wherein the retaining feature of the insert comprises a protrusion, and wherein the complementary retaining feature of at least one of the first and second members comprises a complementary protrusion.

4. The implant of claim 2, wherein the retaining feature of the insert comprises a protrusion having a ramped leading surface and a trailing edge, and wherein the complementary retaining feature comprises a complementary protrusion having a ramped leading surface and a trailing edge,
wherein, during insertion of the insert, the ramped leading surfaces are configured to slidingly engage and move past one another such that the trailing edges engage one another to inhibit movement of the insert relative to the at least one of the first and second members.

5. The implant of claim 4, wherein at least one of the protrusions deflects relative to the other of the protrusions to generate a snap-fit of the trailing edges.

6. The implant of claim 1, wherein engagement of the first and second guide tracks with the first and second guide rails, respectively, inhibits lateral movement of the of the first and second members relative to the insert, and wherein at least one of the first and second guide tracks is configured to interlock with the first and second guide rails, respectively, to inhibit vertical separation of the insert from the first or second member.

7. The implant of claim 1, wherein at least one of the first and second guide tracks comprises a dovetailed groove, and wherein at least one of the first and second guide rails comprises a complementary dovetailed groove configured to interlock with the dovetailed groove.

8. The implant of claim 1, wherein each of the first member, the second member and the insert comprises openings that at least partially align during use to define a vertical opening extending between the exterior surfaces of the first and second members, wherein the vertical opening facilitates bone through growth between the first and second vertebra during use.

9. The implant of claim 1, wherein at least one of the first and second members comprises a stop to limit longitudinal advancement of the insert between the first and second members.

10. The implant of claim 9, wherein the stop comprises a lip configured to engage a complementary lip of the insert.

11. The implant of claim 1, wherein the exterior surfaces of the first and second members each comprises protrusions configured to engage the endplates of the first and second vertebra, respectively, and wherein the protrusions comprise a ramped leading surface and a substantially vertical trailing edge such that the protrusions are configured to facilitate insertion of the first and second members into the intervertebral space and to inhibit removal of the of the first and second members from the intervertebral space.

12. The implant of claim 1, wherein trailing ends of the first and second members comprise tool engagement features configured to be engaged by an insertion tool.

13. The implant of claim 12, wherein the insertion tool engage the tool engagement features during use, and wherein the insertion tool is expanded to distract the first member of the implant relative to the second member of the implant to facilitate insertion of the insert between the first and second members of the implant.

14. The implant of claim 12, wherein the insertion tool comprises a first guide track configured to be engaged by the first guide rail of the insert and a second tool guide track configured to be engaged by the second guide rail of the insert.

15. The implant of claim 12, wherein the insertion tool comprises:
a first tool elongate member comprising:
a distal end configured to couple to a trailing end of the first member; and
a first tool guide track extending longitudinally along the first tool elongate member, wherein the first tool guide track is configured to be engaged by the first guide rail of the insert during use, and wherein the first tool guide track substantially aligns with the first guide track of the upper member of the implant during use;
a second tool elongate member comprising:
a distal end configured to couple to a trailing end of the second member; and
a second tool guide track extending longitudinally along the second tool elongate member, wherein the second tool guide track is configured to be engaged by the second guide rail of the insert during use, and wherein the second tool guide track substantially aligns with the second guide track of the second member of the implant during use.

16. The implant of claim 1, wherein the intervertebral implant is disposed adjacent another intervertebral implant during use.

17. The implant of claim 16, wherein the intervertebral implants are disposed on opposite sides of a sagittal plane of the vertebra during use.

18. A method of implanting an intervertebral implant within an intervertebral space between endplates of adjacent vertebra, comprising:
inserting a first member into the intervertebral space such that an exterior surface of the first member contacts an endplate of a first of the adjacent vertebra, wherein the first member comprises an interior surface comprising a first guide track;
inserting a second member into the intervertebral space such that an exterior surface of the second member contacts an endplate of a second of the adjacent vertebra, wherein the second member comprises an interior surface comprising a second guide track;
inserting, between the first and second members, an insert comprising:
a first exterior surface comprising a first guide rail; and a second exterior surface comprising a second guide rail;

wherein the first guide rail engages the second guide track;

guiding insertion of the insert between the first and second members by engaging the first and second guide rails with the first and second guide tracks, respectively;

expanding the intervertebral implant by inserting the insert between the first and the second members such that a separation distance between the first and the second members is increased;

inhibiting back-out of the insert from between the first and second members by rotating an actuatable locking mechanism from an unlocked position to a locked position such that the insert is coupled to the first and second members;

engaging a first locking recess of the first member and a second locking recess of the second member with one or more members of the locking member when the actuatable locking mechanism is rotated from an unlocked position to a locked position.

19. The implant of claim 6, wherein at least one of the first and second guide rails and at least one of the first and second guide tracks comprise complementarily engaging S shaped profiles.

* * * * *